US008546480B2

(12) United States Patent
Yoshida et al.

(10) Patent No.: US 8,546,480 B2
(45) Date of Patent: Oct. 1, 2013

(54) RELIEF PRINTING PLATE PRECURSOR FOR LASER ENGRAVING AND METHOD FOR PRODUCING RELIEF PRINTING PLATE

(75) Inventors: Kenta Yoshida, Shizuoka-ken (JP); Takashi Kawashima, Shizuoka-ken (JP)

(73) Assignee: FUJIFILM Corporation, Tokyo (JP)

( * ) Notice: Subject to any disclaimer, the term of this patent is extended or adjusted under 35 U.S.C. 154(b) by 416 days.

(21) Appl. No.: 12/749,534

(22) Filed: Mar. 30, 2010

(65) Prior Publication Data

US 2010/0243624 A1 Sep. 30, 2010

(30) Foreign Application Priority Data

Mar. 31, 2009 (JP) ................................ 2009-085072
Mar. 1, 2010 (JP) ................................ 2010-044188

(51) Int. Cl.
*C08L 33/00* (2006.01)
*A61K 9/16* (2006.01)
*G03C 1/00* (2006.01)

(52) U.S. Cl.
USPC ............... 524/543; 524/556; 522/2; 264/400; 430/270.1; 430/286.1; 219/121.69

(58) Field of Classification Search
USPC ......... 428/156; 522/2; 264/400; 430/270.1, 430/281.1, 286.1; 219/121.69; 524/556, 524/543, 547
See application file for complete search history.

(56) References Cited

U.S. PATENT DOCUMENTS 5,798,202 A 8/1998 Cushner et al.
6,171,748 B1 * 1/2001 Tanaka et al. ................. 430/138
6,702,437 B2 * 3/2004 Fujimaki et al. .............. 347/101
2008/0038544 A1 * 2/2008 Kitaike et al. ................ 428/336
2009/0246469 A1 * 10/2009 Kawashima et al. .......... 428/156
2010/0075117 A1 * 3/2010 Kawashima et al. ...... 428/195.1
2011/0156317 A1 * 6/2011 Yoshida ........................ 264/400
2011/0318537 A1 * 12/2011 Yoshida ........................ 428/156
2011/0319563 A1 * 12/2011 Yamashita ...................... 525/61

FOREIGN PATENT DOCUMENTS

JP 2846954 B2 1/1999
JP 2001-121833 A 5/2001
JP 2002-003665 A 1/2002
JP 3438404 B 8/2003
JP 2004-262135 A 9/2004
JP 2005-221655 A 8/2005
JP 2006-002061 A 1/2006

* cited by examiner

*Primary Examiner* — Hannah Pak
(74) *Attorney, Agent, or Firm* — SOLARIS Intellectual Property Group, PLLC

(57) ABSTRACT

A relief printing plate precursor for laser engraving, including a relief forming layer formed by thermally crosslinking a resin composition including (A) a polymer having an ethylenically unsaturated bond in a side chain wherein the polymer is an acrylic resin or a polyvinyl acetal, (B) carbon black, and (C) a thermopolymerization initiator.

6 Claims, No Drawings

RELIEF PRINTING PLATE PRECURSOR FOR LASER ENGRAVING AND METHOD FOR PRODUCING RELIEF PRINTING PLATE

CROSS-REFERENCE TO RELATED APPLICATION

This application claims priority under 35 USC 119 from Japanese Patent Application No. 2009-085072 filed on Mar. 31, 2009 and Japanese Patent Application No. 2010-044188 filed on Mar. 1, 2010, the disclosures of which are incorporated by reference herein.

BACKGROUND OF THE INVENTION

1. Field of the Invention

The present invention relates to a relief printing plate precursor for laser engraving, and a method for producing a relief printing plate.

2. Description of the Related Art

As a method for forming a printing plate by forming concavities and convexities on a photosensitive resin layer laminated on the surface of a support, so-called "analogue plate making," is well known, which is a method comprising exposing a relief forming layer formed using a photosensitive composition to ultraviolet light via an original image film, selectively curing image parts, and removing uncured parts with a developing liquid.

A relief printing plate is an anastatic printing plate having a relief layer with concavities and convexities, and the relief layer with concavities and convexities is obtained by patterning a relief forming layer containing a photosensitive composition containing, as a main component, for example, an elastomeric polymer such as a synthetic rubber, a resin such as a thermoplastic resin, or a mixture of a resin and a plasticizer, and forming concavities and convexities thereon. Among such relief printing plates, one having a flexible relief layer may be referred to as a flexo plate.

In recent years, research has been carried out on a method of performing the plate making of a relief forming layer by scanning exposure, without requiring an original image film as in the case of analogue plate making.

As a technique that does not require an original image film, a relief printing plate precursor provided with a laser-sensitive mask layer element capable of forming an image mask on a relief forming layer, has been proposed (see, for example, U.S. Pat. No. 5,798,202 and Japanese Patent Application Laid-Open (JP-A) No. 2002-3665). According to these methods of plate making of a precursor, since an image mask having the same function as the original image film is formed from a mask layer element by laser irradiation based on image data, these methods are referred to as "mask CTP methods," and original image films are not required. However, the subsequent plate making treatment involves processes of exposure to ultraviolet light through an image mask, and developing and removing uncured parts, and there is a room for further improvement from the viewpoint of the necessity of development treatment.

As a plate making method that does not require a development process, a so-called "direct engraving CTP method" that includes directly engraving a relief forming layer with a laser to carry out plate making, has been proposed in many cases. The direct engraving CTP method is literally a method of forming concavities and convexities that serves as a relief by engraving with a laser, and unlike the relief formation using an original image film, there is an advantage that the relief shape can be freely controlled. Accordingly, in the case of forming images like outline characters, it is possible to engrave the image regions deeper than other regions, and in the case of forming fine halftone dot images, it is possible to carry out shouldered engraving in consideration of resistance to the printing pressure.

In regard to the plate materials that have been so far used in the direct engraving CTP method, many materials have been proposed as the binder that determines the characteristics of the plate materials, such as a material using a hydrophobic elastomer (rubber) (see, for example, U.S. Pat. No. 5,798,202, Japanese Patent Application Laid-Open (JP-A) No. 2002-3665, Japanese Patent No. 3438404, Japanese Patent Application Laid-Open (JP-A) No. 2004-262135 and Japanese Patent Application Laid-Open (JP-A) No. 2001-121833), a material using a hydrophilic polyvinyl alcohol derivative (see, for example, Japanese Patent Application Laid-Open (JP-A) No. 2006-2061), and a material using an elastomer having a crosslinked structure (see, for example, Japanese Patent No. 2846954).

There has been also proposed a method of producing a flexo printing plate precursor having improved film strength and printing durability by photocuring a photosensitive resin composition including a resin having a polymerizable unsaturated group (see, for example, Japanese Patent Application Laid-Open (JP-A) No. 2005-221655).

However, in the above-described techniques, since the sensitivity is low, when concavities and convexities are formed in the relief forming layer so as to have an engraving depth to form a relief that is resistant to the printing pressure, high energy is required. Further, since the laser engraving speed is low, the productivity is low as compared to the case of forming an image through a mask.

As discussed above, various techniques have been proposed in regard to a resin composition that can be suitably used in the relief forming layer of a relief printing plate precursor for laser engraving, but under the current circumstances, a resin composition that exhibits good film strength when formed into a film, and thus provides excellent printing durability of the printing plate formed when the resin composition is applied to the relief forming layer, and further exhibits high engraving sensitivity when subjected to laser engraving, has not yet been provided.

SUMMARY OF THE INVENTION

According to an aspect of the invention, there is provided a relief printing plate precursor for laser engraving, comprising a relief forming layer formed by thermally crosslinking a resin composition comprising (A) a polymer having an ethylenically unsaturated bond in a side chain wherein the polymer is an acrylic resin or a polyvinyl acetal, (B) carbon black, and (C) a thermopolymerization initiator.

DETAILED DESCRIPTION OF THE INVENTION

Hereinafter, the resin composition that is used for the formation of a relief forming layer, a relief forming layer formed by the resin composition, a relief printing plate precursor for laser engraving, and a method for producing a relief printing plate of the present invention will be described in detail.

<Resin Composition>

The resin composition used in the invention contains (A) a polymer having an ethylenically unsaturated bond in a side chain wherein the polymer is an acrylic resin or a polyvinyl acetal, (B) carbon black, and (C) a thermopolymerization initiator, and the resin composition is thermally crosslinked to form a relief forming layer.

Hereinafter, in the invention, a resin composition that is used in the formation of a relief forming layer may be referred to as "composition 1", and a composition that constitutes a relief forming layer formed by thermally crosslinking the composition 1 may be referred to as "composition 2."

Therefore, the composition 2 according to the invention contains (A) a polymer having an ethylenically unsaturated bond in a side chain wherein the polymer is an acrylic resin or a polyvinyl acetal, (B) carbon black, (C) a thermopolymerization initiator, and a compound having a structure in which the (A) polymer having an ethylenically unsaturated bond in a side chain wherein the polymer is an acrylic resin or a polyvinyl acetal is crosslinked [if (D) a crosslinking agent is used, a compound having a structure in which the (A) polymer having an ethylenically unsaturated bond in a side chain wherein the polymer is an acrylic resin or a polyvinyl acetal and the (D) crosslinking agent are crosslinked].

The composition 2 that constitutes a relief forming layer in the relief printing plate precursor of the invention has high engraving sensitivity when applied to laser engraving, and thus allows high speed laser engraving, thereby shortening the engraving time. The composition 2 having such characteristics is not particularly limited and may be widely applied to uses for forming resin molded articles having a relief forming layer on which laser engraving is performed. For example, embodiments of the composition 2 used in the invention include specifically a relief image forming layer of an image forming material on which image formation is carried out by laser engraving, a relief forming layer of a printing plate precursor on which convex-shaped or concave-shaped relief formation is carried out by laser engraving, and the like, but the uses for forming resin molded articles having a relief forming layer are not limited to these.

<(A) Polymer Having an Ethylenically Unsaturated Bond in a Side Chain Wherein the Polymer is an Acrylic Resin or a Polyvinyl Acetal>

The resin composition (composition 1) used in the invention contains (A) a polymer having an ethylenically unsaturated bond in a side chain wherein the polymer is an acrylic resin or a polyvinyl acetal (hereinafter, also referred to as "specific polymer"). The (A) polymer having an ethylenically unsaturated bond in a side chain wherein the polymer is an acrylic resin or a polyvinyl acetal may be a polymer in which the main chain structure is an acrylic resin or a polyvinyl acetal, and a group having a carbon-carbon unsaturated bond, such as an allyl group, an acryloyl group, a methacryloyl group, a styryl group or a vinyl ether group, is introduced in a side chain of the polymer.

A polymer in which the main chain structure is a polyvinyl acetal is preferable in view of engraving sensitivity.

Furthermore, from the viewpoint of rinsability and printing durability when formed into a relief forming layer, the polymer is more preferably a polyvinyl butyral.

The method of introducing a carbon-carbon unsaturated bond into a side chain of the (A) specific polymer may be any known method, such as (i) a method of copolymerizing a structural unit having a polymerizable group precursor that is formed by bonding a protective group to a polymerizable group, in a polymer, and detaching the protective group to obtain a polymerizable group; or (ii) a method of producing a polymer compound having plural reactive groups such as a hydroxyl group, an amino group, an epoxy group and a carboxyl group, and introducing a compound having a group reactive with these reactive groups and a carbon-carbon unsaturated bond into the polymer through a polymer reaction. According to these methods, the amounts of the unsaturated bond and polymerizable group introduced into the polymer compound may be controlled.

When a polymer whose glass transition temperature is higher than 20° C. (room temperature) is used as the (A) specific polymer, the (A) specific polymer is in a glassy state at normal temperature, and for this reason, the thermal molecular movement is quite suppressed as compared with the case where the polymer is in a rubbery state. In the process of laser engraving, the heat given by the laser during laser irradiation as well as the heat generated by the function as a photothermal converting agent of the (B) carbon black are transferred to the (A) specific polymer present in the surroundings, and this specific polymer is thermally decomposed and dissipates to result in engraved concave parts being formed.

The upper limit of the glass transition temperature of the (A) specific polymer is not limited, but is preferably 200° C. or lower from the viewpoint of handlability.

According to a preferred embodiment of the invention, it is considered that when (B) carbon black is present in a state in which the thermal molecular movement of (A) specific polymer has been suppressed, the heat transfer to the (A) specific polymer and thermal decomposition occur effectively, and it is considered that the engraving sensitivity is even more enhanced by such an effect.

The glass transition temperature (Tg) in the invention is measured using a differential scanning calorimeter (DSC). Specifically, 10 mg of a sample is placed on a measurement pan, heated from 30° C. to 250° C. at a rate of 10° C./min in a nitrogen gas stream (1st-run), and then is cooled to 0° C. at a rate of 10° C./min. Subsequently, the sample is heated again from 0° C. to 250° C. at a rate of 10° C./min (2nd-run). The temperature at which the baseline begins to shift from the low temperature side in the 2nd-run is defined as the glass transition temperature (Tg).

(Acrylic Resin)

The acrylic resin that may be used as the (A) specific polymer in the invention may be any acrylic resin that is obtained using a known acrylic monomer, and has an ethylenically unsaturated bond in a side chain.

The method of obtaining an acrylic resin having an ethylenically unsaturated bond in a side chain may be a method of reacting an acrylic resin having a hydroxyl group in the molecule, with a compound having an ethylenically unsaturated group and a group reactive with a hydroxyl group (for example, a compound having an ethylenically unsaturated bond and an epoxy ring, such as glycidyl acrylate; a compound having an ethylenically unsaturated bond and an isocyanate group, such as allyl isocyanate; or the like), or the like.

The acrylic resin having a hydroxyl group may be obtained by copolymerizing an acrylic monomer having a hydroxyl group with an acrylic monomer having another structure, or the like.

Suitable examples of the acrylic monomer having a hydroxyl group include any monomers having a hydroxyl group in the molecule, such as (meth)acrylic acid esters, crotonic acid esters and (meth)acrylamides, and specific examples include 2-hydroxyethyl (meth)acrylate, 2-hydroxypropyl(meth)acrylate, 4-hydroxybutyl(meth)acrylate, and the like.

The acrylic monomer having another structure is an acrylic monomer other than the acrylic monomer having a hydroxyl group, and examples of such an acrylic monomer include, as (meth)acrylic acid esters, methyl(meth)acrylate, ethyl(meth) acrylate, n-propyl (meth)acrylate, isopropyl(meth)acrylate, n-butyl(meth)acrylate, isobutyl(meth)acrylate, tert-butyl (meth)acrylate, n-hexyl(meth)acrylate, 2-ethylhexyl(meth) acrylate, acetoxyethyl (meth)acrylate, phenyl(meth)acrylate, 2-methoxyethyl(meth)acrylate, 2-ethoxyethyl (meth)acrylate, 2-(2-methoxyethoxy)ethyl(meth)acrylate, cyclohexyl (meth)acrylate, benzyl (meth)acrylate, diethylene glycol monomethyl ether (meth)acrylate, diethylene glycol monoethyl ether (meth)acrylate, diethylene glycol monophenyl ether (meth)acrylate, triethylene glycol monomethyl ether (meth)acrylate, triethylene glycol monoethyl ether (meth) acrylate, dipropylene glycol monomethyl ether (meth)acrylate, polyethylene glycol monomethyl ether (meth)acrylate, polypropylene glycol monomethyl ether (meth)acrylate, monomethyl ether (meth)acrylate of a copolymer of ethylene glycol and propylene glycol, N,N-dimethylaminoethyl (meth)acrylate, N,N-diethylaminoethyl(meth)acrylate, N,N-dimethylaminopropyl (meth)acrylate, and the like.

The weight average molecular weight (determined by GPC measurement using polystyrene standards) of the acrylic resin having an ethylenically unsaturated bond in a side chain is preferably 5,000 to 500,000, more preferably 10,000 to 400,000, and more preferably 15,000 to 300,000. When the weight average molecular weight is 5,000 or more, the shape maintainability as a simple resin is excellent, and when the weight average molecular weight is 500,000 or less, the resin is easily dissolved in a solvent, and is suitable for the preparation of a resin composition for laser engraving.

(Polyvinyl Acetal)

Polyvinyl acetal is a compound obtainable by cyclic acetalizing a polyvinyl alcohol (obtained by saponifying a polyvinyl acetate), and is a polymer containing a hydroxyl group in a side chain.

A polyvinyl acetal having an ethylenically unsaturated bond in a side chain may be obtained by a method of reacting the hydroxyl group in the side chain with a compound having an ethylenically unsaturated bond and a group that reacts with a hydroxyl group in the same manner as described in the section for acrylic resin.

The acetal content in the polyvinyl acetal (mole percent of the vinyl alcohol unit that is acetalized, when the total number of moles of the raw material vinyl acetate monomer is taken as 100%) is preferably 30% to 90%, more preferably 50% to 85%, and particularly preferably 55% to 78%.

The vinyl alcohol unit in the polyvinyl acetal is preferably 10 mol % to 70 mol %, more preferably 15 mol % to 50 mol %, and particularly preferably 22 mol % to 45 mol %, relative to the total number of moles of the raw material vinyl acetate monomer.

The polyvinyl acetal may also have a vinyl acetate unit as another component, and the content thereof is preferably 0.01 to 20 mol %, and more preferably 0.1 to 10 mol %. The polyvinyl acetal may further have another copolymerizable unit.

Examples of the polyvinyl acetal include polyvinyl butyral, polyvinyl propyral, polyvinyl ethyral, polyvinyl methyral, and the like. Among them, polyvinyl butyral is preferably used.

As the aldehyde used in the acetal treatment, acetaldehyde and butyl aldehyde are preferably used due to their easy handlability.

The weight average molecular weight (determined by GPC measurement using polystyrene standards) of the polyvinyl acetal having an ethylenically unsaturated bond in a side chain is preferably 5,000 to 500,000, more preferably 10,000 to 400,000, and even more preferably 15,000 to 300,000. When the weight average molecular weight is 5,000 or more, the shape maintainability as a simple resin is excellent, and when the weight average molecular weight is 500,000 or less, the resin is easily dissolved in a solvent, and is suitable for the preparation of a resin composition for laser engraving.

As the polyvinyl butyral, the DENKA BUTYRAL series manufactured by Denki Kagaku Kogyo Kabushiki Kaisha may be preferably used.

As the polyvinyl butyral, other commercially available products may also be purchased, and specific preferable examples thereof include the "S-LEC B" series and "S-LEC K (KS)" series manufactured by Sekisui Chemical Co., Ltd., which are also preferable from the viewpoint of alcohol solubility (particularly, ethanol). More preferable examples include the "S-LEC B" series manufactured by Sekisui Chemical Co., Ltd., and the "DENKA BUTYRAL" manufactured by Denki Kagaku Kogyo Kabushiki Kaisha, from the viewpoint of alcohol solubility (particularly, ethanol), and particularly preferable examples include "BL-1", "BL-1H", "BL-2", "BL-5", "BL-S", "BX-L", "BM-S", "BH-S" of the "S-LEC B" series; "#3000-1", "#3000-2", "#3000-4", "#4000-2", "#6000-C", "#6000-EP", "#6000-CS", and "#6000-AS" of the "DENKA BUTYRAL" manufactured by Denki Kagaku Kogyo Kabushiki Kaisha.

From the viewpoint of the engraving sensitivity, the (A) specific polymer used in the invention preferably has a carbon-heteroatom bond between the main chain and the ethylenically unsaturated bond in a side chain, and the carbon-heteroatom bond is particularly preferably a carbon-sulfur bond.

Examples of the method of introducing a carbon-heteroatom bond (particularly, a carbon-sulfur bond) between the main chain and the ethylenically unsaturated bond in the side chain in the specific polymer include a synthetic method of reacting an acrylic resin having a hydroxyl group in the molecule or a polyvinyl acetal, with a compound which has an ethylenically unsaturated bond and a group that reacts with a hydroxyl group, and further has a heteroatom (particularly, a sulfur atom) between the ethylenically unsaturated bond and the group that reacts with a hydroxyl group.

The content of the ethylenically unsaturated bond in a side chain in the (A) specific polymer (which may be any of the above-described polymers) according to the invention is preferably 0.1 to 15 mmol/g, and more preferably 0.5 to 7 mmol/g, from the viewpoint of physical properties of the film.

Specific examples of the specific polymer used in the invention will be shown below, but the invention is not intended to be limited to these compounds.

Among the exemplary compounds of the invention, each of P-1 to P-12 represents a polymer that is synthesized by modifying 50 mol % of the hydroxyl groups of the polyvinyl acetal with the substituent represented by the following P-1 to P-12. The symbol * in the following structures indicates that the structure is bonded to an oxygen atom at this position.

Furthermore, each of P-13 to P-17 represents an acrylic resin-based specific polymer containing the following structural units at the molar ratio indicated below.

The weight average molecular weights and glass transition temperatures (Tg) of P-1 to P-17 will be presented in Table 1. A polymer having a glass transition temperature in the range of 20° C. to 200° C. is indicated with the symbol "O", while a polymer having a glass transition temperature of below 20° C. or above 200° C. is indicated with the symbol "X".

P-1

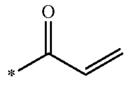

-continued
P-2
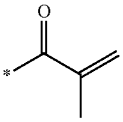
P-3
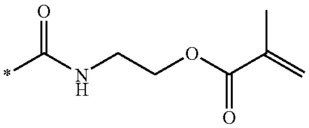
P-4
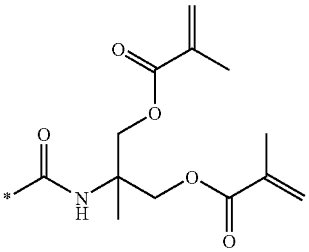
P-5
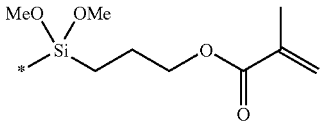
P-6
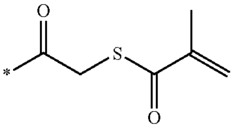
P-7
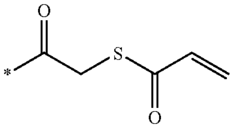
P-8
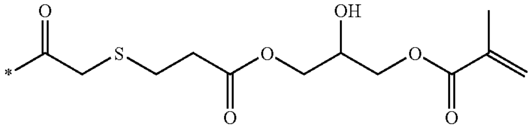
P-9
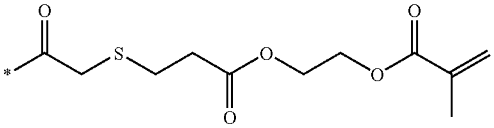
P-10
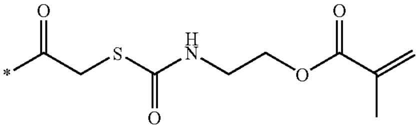
P-11
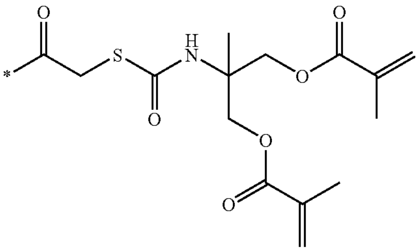
-continued
P-12
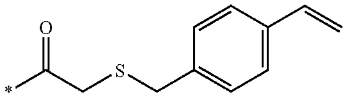
P-13
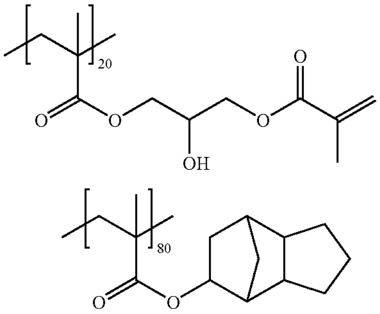
P-14
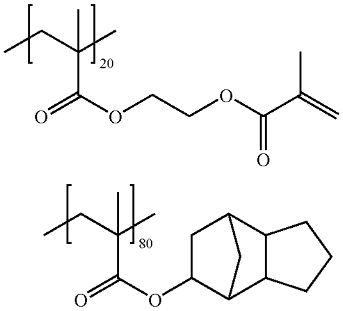
P-15
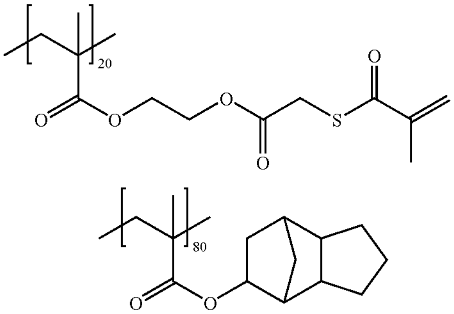
P-16
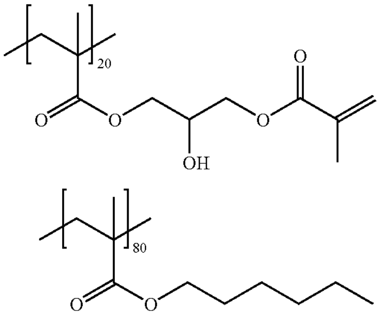
P-17
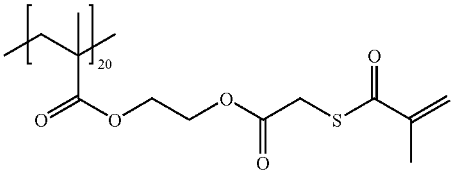

-continued

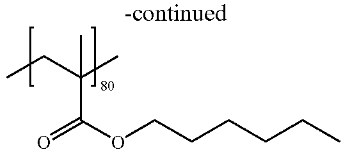

TABLE 1

| Specific polymer | Weight average molecular weight | Tg |
|---|---|---|
| P-1 | 90,000 | ○ |
| P-2 | 90,000 | ○ |
| P-3 | 90,000 | ○ |
| P-4 | 90,000 | ○ |
| P-5 | 90,000 | ○ |
| P-6 | 90,000 | ○ |
| P-7 | 90,000 | ○ |
| P-8 | 90,000 | ○ |
| P-9 | 90,000 | ○ |
| P-10 | 90,000 | ○ |
| P-11 | 90,000 | ○ |
| P-12 | 90,000 | ○ |
| P-13 | 50,000 | ○ |
| P-14 | 50,000 | ○ |
| P-15 | 50,000 | ○ |
| P-16 | 50,000 | X |
| P-17 | 50,000 | X |

The content of the (A) specific polymer according to the invention is preferably 5 mass % to 80 mass %, more preferably 15 mass % to 75 mass %, and even more preferably 20 mass % to 65 mass %, based on the total mass (solid content) of the resin composition (composition 1).

For example, when the resin composition of the invention is applied to a relief forming layer of a relief printing plate precursor, printing durability sufficient for the use of the obtained relief printing plate as a printing plate is obtained by adjusting the content of the specific polymer to 15 mass % or more. Furthermore, by adjusting the content to 75 mass % or less, there is no insufficiency in other components, and sufficient flexibility for use in a printing plate may be obtained even when the relief printing plate is used as a flexo printing plate.

<(B) Carbon Black>

The composition 1 used in the invention contains (B) carbon black. Here, carbon black is an agent functioning as a photothermal converting agent, and it is considered that when this component absorbs the light from a laser and generates heat, thermal decomposition of a cured product of the relief forming layer (relief forming layer after crosslinking) is accelerated.

In regard to the carbon black, all products may be used regardless of the classification by ASTM as well as the applications (for example, color applications, rubber applications, dry cell applications, and the like), so long as dispersibility in the composition 1 is stable. Examples of the carbon black include furnace black, thermal black, channel black, lamp black, acetylene black, and the like. Black-colored materials such as carbon black may be used as color chips or color pastes in which the materials have been dispersed in nitrocellulose, a binder or the like in advance, optionally using a dispersant in order to facilitate dispersion. Such chips or pastes may be easily purchased as commercially marketed products.

According to the invention, it is also possible to use a carbon black having a relatively small specific surface area and a relatively small DBP oil absorption amount, or even a finely divided carbon black having a large specific surface area. Suitable examples of the carbon black include PRINTEX (registered trademark) U, PRINTEX (registered trademark) A, or SPEZIALSCHWARZ (registered trademark) 4 (all manufactured by Degussa Co.).

As the carbon black that is applicable to the invention, conductive carbon black is preferable from the viewpoint that the engraving sensitivity is enhanced by efficiently transferring the heat generated by photothermal conversion to the polymer and the like in the surroundings.

The specific surface area may be 150 $m^2/g$ or larger, preferably 250 $m^2/g$ or larger, and particularly preferably 500 $m^2/g$ or larger. The DBP oil absorption amount is preferably 150 ml/100 g or more, preferably 200 ml/100 g or more, and particularly preferably 250 ml/100 g or more.

The carbon black described above may be acidic or basic, but is preferably basic carbon black.

An appropriate conductive carbon black having a specific surface area reaching up to about 1500 $m^2/g$ and a DBP oil absorption amount reaching up to about 550 ml/100 g, is commercially available under the names of, for example, KETJENBLACK (registered trademark) EC300J, KETJENBLACK (registered trademark) EC600J (from Akzo), PRINTEX (registered trademark) XE (from Degussa), or BLACK PEARLS (registered trademark) 2000 (from Cabot), and KETJENBLACK (manufactured by Lion Corp.).

In the composition 1, the content of the (B) carbon black may be 0.01 mass % to 20 mass %, and preferably 0.1 mass % to 5 mass %, based on the solid content of the composition 1. When the content is in this range, the engraving sensitivity is good.

<(C) Polymerization Initiator>

The composition 1 used in the invention further contains a (C) thermopolymerization initiator.

Any thermopolymerization initiator that is known to those skilled in the art may be used without limitation. Hereinafter, a radical polymerization initiator, which is a preferable thermopolymerization initiator, will be described in detail, but the invention is not intended to be limited by these descriptions.

According to the invention, preferable examples of the radical polymerization initiator used as a thermopolymerization initiator include an organic peroxide and an azo compound.

Use of an organic peroxide or an azo compound enables high engraving sensitivity and a good relief edge shape when applied to a relief forming layer of a relief printing plate precursor.

Of these, an organic peroxide is particularly preferable.

As the organic peroxide and the azo compound, the compounds shown below are preferable, but the invention is not limited thereto.

(Organic Peroxide)

Examples of the organic peroxide preferable as the radical polymerization initiator that may be used as a thermopolymerization initiator in the invention include peroxy esters such as 3,3',4,4'-tetra(tertiary butylperoxycarbonyl)benzophenone, 3,3',4,4'-tetra(tertiary amylperoxycarbonyl)benzophenone, 3,3',4,4'-tetra(tertiary hexylperoxycarbonyl)benzophenone, 3,3',4,4'-tetra(tertiary octylperoxycarbonyl) benzophenone, 3,3',4,4'-tetra(cumylperoxycarbonyl) benzophenone, 3,3',4,4'-tetra(p-isopropylcumylperoxycarbonyl)benzophenone, and di-tertiary butyl diperoxyisophthalate.

(Azo Compound)

Examples of the azo compound preferable as the radical polymerization initiator that may be used as a thermopolymerization initiator in the invention include 2,2'-azobisisobutyronitrile, 2,2'-azobispropionitrile, 1,1'-azobis(cyclohexane-1-carbonitrile), 2,2'-azobis(2-methylbutyronitrile), 2,2'-azobis(2,4-dimethylvaleronitrile), 2,2'-azobis(4-methoxy-2,4-dimethylvaleronitrile), 4,4'-azobis(4-cyanovaleric acid), dimethyl 2,2'-azobisisobutyrate, 2,2'-azobis(2-methylpropionamidoxime), 2,2'-azobis[2-(2-imidazolin-2-yl)propane], 2,2'-azobis{2-methyl-N-[1,1-bis(hydroxymethyl)-2-hydroxyethyl]propionamide}, 2,2'-azobis[2-methyl-N-(2-hydroxyethyl)propionamide], 2,2'-azobis(N-butyl-2-methylpropionamide), 2,2'-azobis(N-cyclohexyl-2-methylpropionamide), 2,2'-azobis[N-(2-propenyl)-2-methylpropionamide], 2,2'-azobis(2,4,4-trimethylpentane), and the like.

The (C) thermopolymerization initiators according to the present invention may be used individually, or may also be used in combination of two or more types.

The (C) thermopolymerization initiator may be added preferably at a proportion of 0.01 to 10 mass %, and more preferably 0.1 to 3 mass %, based on the total solid content of the composition 1.

<(D) Crosslinking Agent>

According to the invention, from the viewpoint of forming a crosslinked structure in the relief forming layer, the composition 1 preferably contains a (D) crosslinking agent according to necessity.

Any crosslinking agent may be used in the invention without particular limitation, so long as the agent is capable of polymerizing through a chemical reaction induced by heat and curing a relief forming layer. In particular, a polymerizable compound having an ethylenically unsaturated double bond (hereinafter, also referred to as “polymerizable compound”), a silane coupling agent, and the like are preferably used. These compounds may form a crosslinked structure in the relief forming layer by reacting with the specific polymer, may form a crosslinked structure when these compounds react with each other, or may form a crosslinked structure by both of these reactions.

Here, as the polymerizable compound that may be used, any compound may be selected from compounds having at least one, preferably two or more, and more preferably 2 to 6 ethylenically unsaturated double bonds.

Hereinafter, a monofunctional monomer having one ethylenically unsaturated double bond in the molecule, and a polyfunctional monomer having two or more ethylenically unsaturated double bonds in the molecule, which are used as the polymerizable compound, will be explained.

Since the relief forming layer according to the invention needs to have a crosslinked structure in the film, a polyfunctional monomer is preferably used. The molecular weight of such a polyfunctional monomer is preferably 200 to 2000.

Examples of the monofunctional monomer include esters of unsaturated carboxylic acids (for example, acrylic acid, methacrylic acid, itaconic acid, crotonic acid, isocrotonic acid, maleic acid, and the like) and monohydric alcohol compounds, amides of unsaturated carboxylic acids and monovalent amine compounds, and the like.

Examples of the polyfunctional monomer include esters of unsaturated carboxylic acids (for example, acrylic acid, methacrylic acid, itaconic acid, crotonic acid, isocrotonic acid, maleic acid, and the like) and polyhydric alcohol compounds, amides of unsaturated carboxylic acids and polyvalent amine compounds, and the like.

Preferable examples also include addition reaction products of an unsaturated carboxylic acid ester or amide having a nucleophilic substituent group such as a hydroxyl group, an amino group or a mercapto group with a monofunctional or polyfunctional isocyanate or epoxy compound, and dehydration condensation products thereof with a monofunctional or polyfunctional carboxylic acid.

Preferable examples further include addition reaction products of an unsaturated carboxylic acid ester or amide having an electrophilic substituent group such as an isocyanate group or an epoxy group with a monofunctional or polyfunctional alcohol, amine or thiol, and substitution reaction products of an unsaturated carboxylic acid ester or amide having an elimination substitution group such as a halogen group or a tosyloxy group with a monofunctional or polyfunctional alcohol, amine or thiol.

Other examples include the above compounds in which an unsaturated phosphonic acid, styrene, vinyl ether, or the like is used in place of the unsaturated carboxylic acid.

The polymerizable compound is not specifically limited, and other than the above described compounds, various known compounds may be used, examples of which include compounds described in paragraphs [0098] to [0124] in JP-A No. 2009-204962.

According to the invention, it is preferable to use a compound having a sulfur atom in the molecule as the polymerizable compound, from the viewpoint of enhancing the engraving sensitivity.

As the polymerizable compound having a sulfur atom in the molecule, it is particularly preferable to use a polymerizable compound having two or more ethylenically unsaturated bonds, and having a carbon-sulfur bond at the site linking between two of the ethylenically unsaturated bonds (hereinafter, appropriately referred to as “sulfur-containing polyfunctional monomer”), from the viewpoint of enhancing the engraving sensitivity.

The functional group containing a carbon-sulfur bond in the sulfur-containing polyfunctional monomer according to the invention may be a functional group containing sulfide, disulfide, sulfoxide, sulfonyl, sulfonamide, thiocarbonyl, thiocarboxylic acid, dithiocarboxylic acid, sulfamic acid, thioamide, thiocarbamate, dithiocarbamate, or thiourea.

The linking group containing a carbon-sulfur bond and linking between two ethylenically unsaturated bonds in the sulfur-containing polyfunctional monomer is preferably at least one unit selected from —C—S—, —C—SS—, —NH(C═S)O—, —NH(C═O)S—, —NH(C═S)S— and —C—$SO_2$—.

The number of sulfur atoms contained in the molecule of the sulfur-containing polyfunctional monomer is not particularly limited so long as it is one or greater, and may be appropriately selected according to the purpose. However, from the viewpoint of balancing the engraving sensitivity and the solubility in coating solvents, the number of sulfur atoms is preferably 1 to 10, more preferably 1 to 5, and more preferably 1 or 2.

On the other hand, the number of ethylenically unsaturated sites contained in the molecule is not particularly limited, so long as the number is two or greater, and may be appropriately selected according to the purpose. However, from the viewpoint of flexibility of the crosslinked film, the number is preferably 2 to 10, more preferably 2 to 6, and even more preferably 2 to 4.

The molecular weight of the sulfur-containing polyfunctional monomer according to the invention is preferably 120 to 3000, and more preferably 120 to 1500, from the viewpoint of flexibility of the film formed.

The sulfur-containing polyfunctional monomers according to the invention may be used individually, but may also be used as mixtures with polyfunctional polymerizable compounds or monofunctional polymerizable compounds that do not have sulfur atoms in the molecule.

Specific examples of polymerizable compounds containing a surfer atom in the molecular include compounds described in paragraphs [0032] to [0037] in JP-A No. 2009-255510, and these compounds may be used in the present invention.

From the viewpoint of engraving sensitivity, an embodiment of using the sulfur-containing polyfunctional monomer alone, or using a mixture of the sulfur-containing polyfunctional monomer and a monofunctional ethylenic monomer is preferable, and an embodiment of using a mixture of the sulfur-containing polyfunctional monomer and a monofunctional ethylenic monomer is more preferable.

In regard to the relief forming layer according to the invention, the film properties such as, for example, brittleness and flexibility, may be adjusted by using a polymerizable compound including the sulfur-containing polyfunctional monomer.

The total content of the polymerizable compound including the sulfur-containing polyfunctional monomer in the relief forming layer is preferably in the range of 10 mass % to 60 mass %, and more preferably 15 mass % to 45 mass %, based on the non-volatile components, from the viewpoint of the flexibility or brittleness of the crosslinked film.

In the case of using the sulfur-containing polyfunctional monomer and another polymerizable compound in combination, the amount of the sulfur-containing polyfunctional monomer in the total polymerizable compounds is preferably 5 mass % or more, and more preferably 10 mass % or more.

In the case of forming a crosslinked structure using a polymerizable compound, it is preferable to use a thermopolymerization initiator. Particularly, it is preferable to use the thermopolymerization initiator in combination, from the viewpoint of enhancing the degree of crosslinking. By enhancing the degree of crosslinking, the quality of engraved images may be enhanced.

It is also preferable to use a silane coupling agent as the (D) crosslinking agent for the invention. According to the invention, a functional group in which at least one alkoxy group or halogen group is directly bonded to a silicon (Si) atom is called a silane coupling group, and a compound having one or more silane coupling groups in the molecule is called a silane coupling agent. The silane coupling group is preferably such that two or more alkoxy groups or halogen atoms are directly bonded to a Si atom, and particularly preferably such that three or more are directly bonded.

It is essential that the silane coupling agent according to the invention has at least one or more functional groups selected from an alkoxy group and a halogen atom as the functional group directly bonded to the Si atom, and from the viewpoint of easy handlability of the compound, it is preferable that the agent have an alkoxy group.

Here, the alkoxy group is preferably an alkoxy group having 1 to 30 carbon atoms from the viewpoint of rinsability and printing durability, and the alkoxy group is more preferably an alkoxy group having 1 to 15 carbon atoms, and particularly preferably an alkoxy group having 1 to 5 carbon atoms.

The halogen atom may be a fluorine (F) atom, a chlorine (Cl) atom, a bromine (Br) atom, or an iodine (I) atom, and from the viewpoints of ease of synthesis and stability, the halogen atom is preferably a Cl atom or a Br atom, and particularly preferably a Cl atom.

The silane coupling agent according to the invention preferably contains one or more and 10 or less silane coupling groups in the molecule, more preferably one or more and 5 or less silane coupling groups, and particularly preferably 2 or more and 4 or less silane coupling groups, from the viewpoint of maintaining the balance between the degree of crosslinking and flexibility of the film favorably.

When there are two or more silane coupling groups, it is preferable that the silane coupling groups be linked by a linking group. The linking group may be a divalent or higher-valent organic group which may be substituted with a substituent such as a heteroatom or a hydrocarbon. An embodiment such that the linking group includes a heteroatom (N, S or O) is preferable in view of having high engraving sensitivity, and the linking group is particularly preferably a linking group containing a S atom.

From such a viewpoint, the silane coupling agent according to the invention is suitably a compound having in the molecule two silane coupling groups in which a methoxy group or ethoxy group as an alkoxy group, and particularly a methoxy group, is bonded to a Si atom, wherein these silane coupling groups are linked via an alkylene group containing a heteroatom, particularly preferably a S atom. More specifically, a silane coupling agent that has a linking group containing a sulfide group is preferred.

As another preferable linking group that links silane coupling groups, a linking group having an oxyalkylene group is exemplified. When the linking group includes an oxyalkylene group, the rinsability of the engraving waste after laser engraving may be improved. The oxyalkylene group is preferably an oxyethylene group, and more preferably a polyoxyethylene chain, in which plural oxyethylene groups are linked. The total number of the oxyethylene groups in the polyoxyethylene chain is preferably 2 to 50, more preferably 3 to 30, and particularly preferably 4 to 15.

Specific examples of the silane coupling agent that is applicable to the invention include vinyltrichlorosilane, vinyltrimethoxysilane, vinyltriethoxysilane, β-(3,4-epoxycylohexyl)ethyltrimethoxysilane, γ-glycidoxypropyltrimethoxysilane, γ-glycidoxypropylmethyldiethoxysilane, γ-glycidoxypropyltriethoxysilane, γ-methacryloxypropylmethyldimethoxysilane, γ-methacryloxypropyltrimethoxysilane, γ-methacryloxypropylmethyldiethoxysialne, γ-methacryloxypropyltriethoxysilane, γ-acryloxypropyltrimethoxysilane, N-(β-aminoethyl)-γ-aminopropylmethyldimethoxysilane, N-(β-aminoethyl)-γ-aminopropyltrimethoxysilane, N-(β-aminoethyl)-γ-aminopropyltriethoxysilane, γ-aminopropyltrimethoxysilane, γ-aminopropyltriethoxysilane, N-phenyl-γ-aminopropyltrimethoxysilane, γ-mercaptopropyltrimethoxysilane, γ-chloropropyltrimethoxysilane, γ-ureidopropyltriethoxysilane, bis(triethoxysilylpropyl)disulfide, bis(triethoxysilylpropyl)tetrasulfide, 1,4-bis(triethoxysilyl)benzene, bis(triethoxysilyl)ethane, 1,6-bis(trimethoxysilyl)hexane, 1,8-bis(triethoxysilyl)octane, 1,2-bis(trimethoxysilyl)decane, bis(triethoxysilylpropyl)amine, bis(trimethoxysilylpropyl)urea, and the like. In addition to the above mentioned silane coupling agents, compounds represented by formulas shown below are preferably exemplified. However, the invention is not restricted to these compounds.

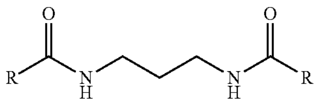
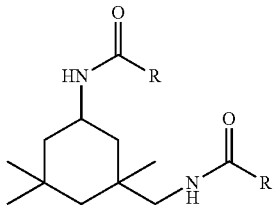
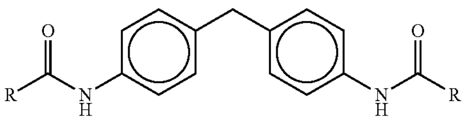
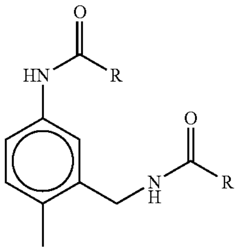
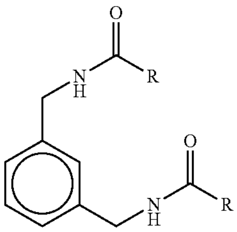
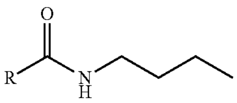
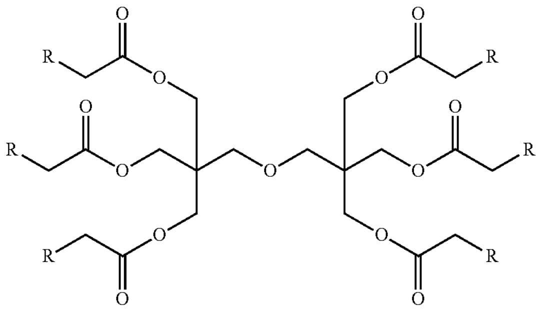
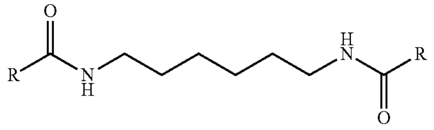
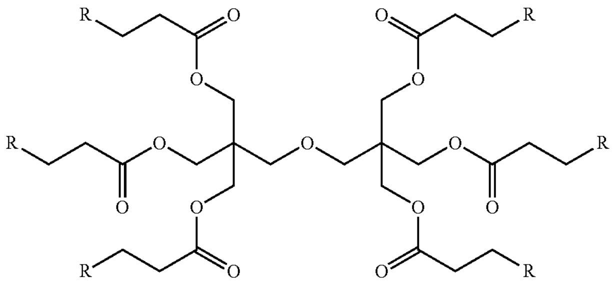
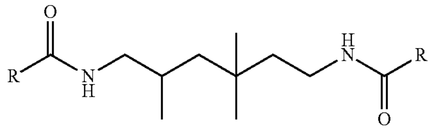
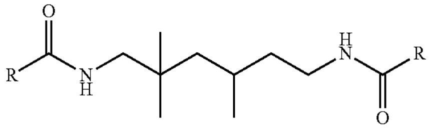
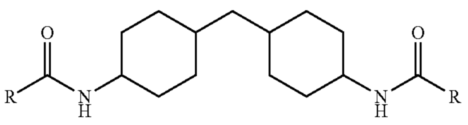
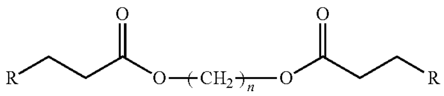
n = 2~20
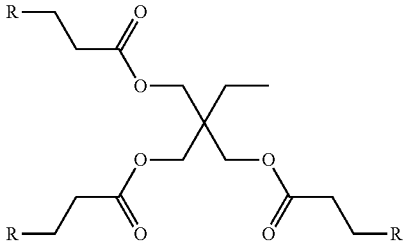
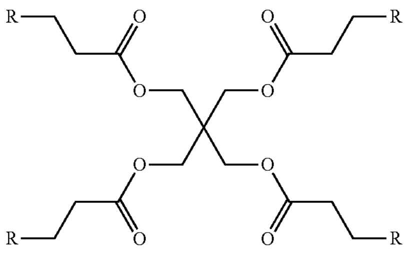
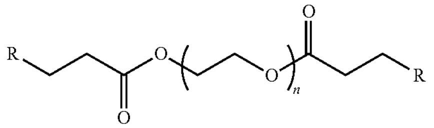
n = 1~50

-continued
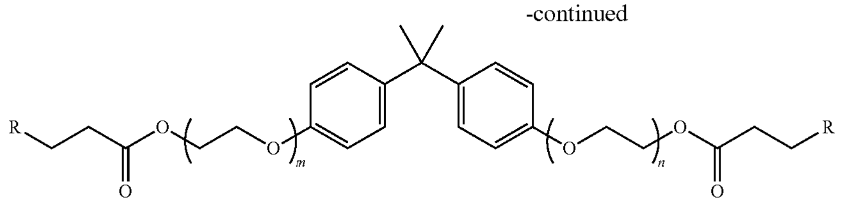
m + n = 2~50
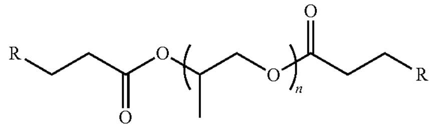
n = 1~50
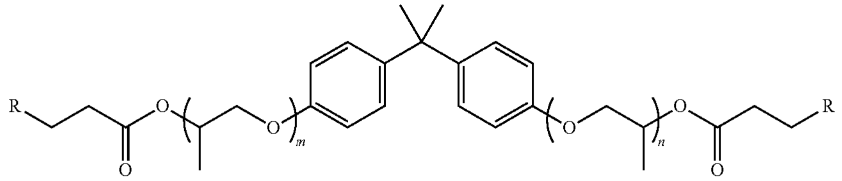
m + n = 2~50
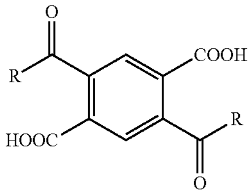
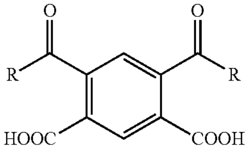
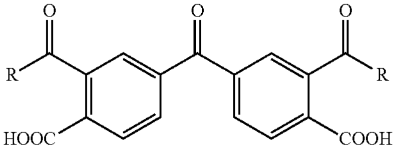
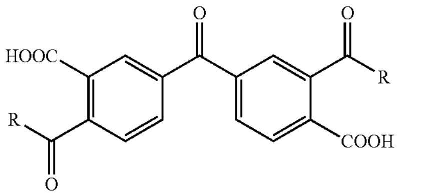
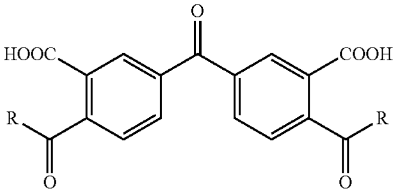
R—S—S—R
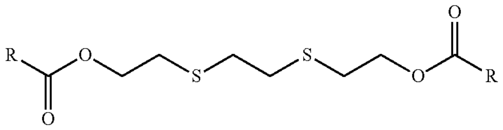
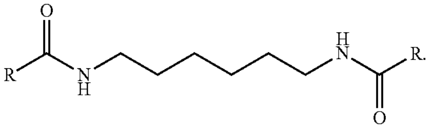
In the above respective formulas, R represents a partial structure selected from structures shown below. When plural Rs and $R^1$s are present in a molecule, these may be same or different from each other. However, these are preferably same from the viewpoint of synthesis suitability.
R: 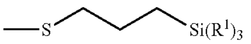 or
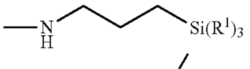 $R^1$: —OMe, —OEt,
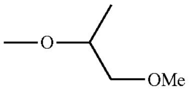 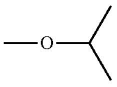 ,
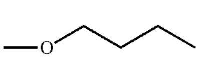 or 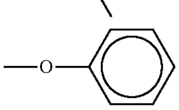
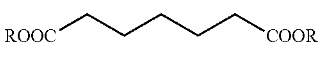 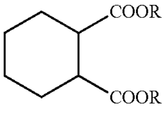
-continued
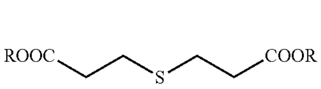 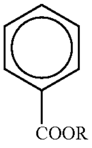
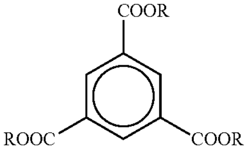 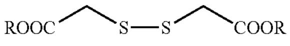
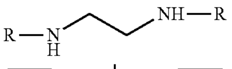
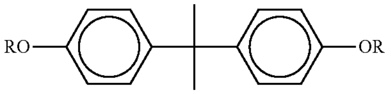
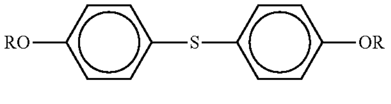

-continued

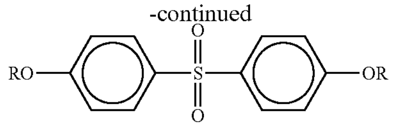

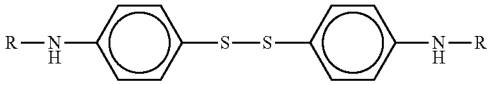

In the above respective formulas, R represents a partial structure shown below. R' is the same as mentioned above. When plural Rs and $R^1$s are present in a molecule, these may be same or different from each other. However, these are preferably same from the viewpoint of synthesis suitability.

R:

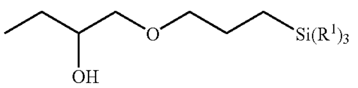

These silane coupling agents may be obtained by appropriately synthesizing. However, commercially available products are preferably used from the viewpoint of cost. Commercially available products such as silane products and silane coupling agents available from Shin-Etsu Chemical Co., Ltd., Dow Corning Toray Silicones Co., Ltd., Momentive Performance Materials, Inc., Chisso Corporation correspond to the silane coupling agents. Accordingly, for a composition of the invention, these commercially available products may be appropriately selected and used in accordance with the object.

As the silane coupling agent in the invention, other than the compounds mentioned above, a partially hydrolyzed condensate obtained from one silane and a partially co-hydrolyzed condensate obtained from two or more kinds of silanes may be used. Hereinafter, these compounds are referred to as "partially (co)hydrolyzed condensate" in some cases.

Specific examples of the partially (co)hydrolyzed condensate include partially (co)hydrolyzed condensates obtained by using, as a precursor, one or more selected from silane compounds including alkoxysilanes such as tetramethoxysilane, tetraethoxysilane, methyltrimethoxysilane, methyltriethoxysilane, methyltriisopropoxysilane, methyltriacetoxysilane, methyltris(methoxyethoxy)silane, methyltris(methoxypropoxy)silane, ethyltrimethoxysilane, propyltrimethoxysilane, butyltrimethoxysilane, hexyltrimethoxysilane, octyltrimethoxysilane, decyltrimethoxysilane, cyclohexyltrimethoxysilane, phenyltrimethoxysilane, phenyltriethoxysilane, tolyltrimethoxysilane, chloromethyltrimethoxysilane, γ-chloropropyltrimethoxysilane, 3,3,3-trifluoropropyltrimethoxysilane, cyanoethyltriethoxysilane, γ-glycidoxypropyltrimethoxysilane, γ-glycidoxypropyltriethoxysilane, β-(3,4-epoxycyclohexyl)ethyltrimethoxysilane, γ-aminopropyltrimethoxysilane, γ-aminopropyltriethoxysilane, N-β(aminoethyl)γ-aminopropyltrimethoxysilane, N-phenyl-γ-aminopropyltrimethoxysilane, γ-mercaptopropyltrimethoxysilane, dimethyldimethoxysilane, dimethyldiethoxysilane, diethyldimethoxysilane, methylethyldimethoxysilane, methylpropyldimethoxysilane, diphenyldimethoxysilane, diphenyldiethoxysilane, methylphenyldimethoxysilane, γ-chloropropylmethyldimethoxysilane, 3,3,3-trifluoropropylmethyldimethoxysilane, γ-glycidoxypropylmethyldiethoxysilane, γ-aminopropylmethyldiethoxysilane, N-β(aminoethyl)γ-aminopropylmethyldimethoxysilane, and γ-mercaptopropylmethyldiethoxysilane, and acyloxysilanes such as acetyloxysilane and ethoxalyloxysilane.

Among the silane compounds as a precursor of the partially (co)hydrolyzed condensate, silane compounds having a substituent selected from a methyl group and a phenyl group as a substituent on a silicon atom are preferred from the viewpoint of general versatility, cost and compatibility of a film. Preferable examples of the silane compound as the precursor specifically include methyltrimethoxysilane, methyltriethoxysilane, phenyltrimethoxysilane, phenyltriethoxysilane, dimethyldimethoxysilane, dimethyldiethoxysilane, diphenyldimethoxysilane, and diphenyldiethoxysilane.

In this case, as the partially (co)hydrolyzed condensate, dimer (disiloxane unit obtained by reacting 1 mole of water with 2 moles of silane compound to eliminate 2 moles of alcohol) to 100 mer, preferably dimer to 50 mer and more preferably dimer to 30 mer of the silane compounds such as mentioned above may be suitably used. Furthermore, a partially (co)hydrolyzed condensate obtained from two or more kinds of silane compounds as a raw material may be used.

As such a partially (co)hydrolyzed condensate, commercially available silicon alkoxy oligomers (for example, ones commercially available from Shin-Etsu Chemical Co., Ltd.) or products produced according to an ordinary method in such a manner that hydrolyzing water less than equivalent to a hydrolyzable silane compound is reacted with the hydrolyzable silane compound and thereafter by-products such as alcohol or hydrochloric acid are removed may be used. At the time of production, when, as a raw material hydrolyzable silane compound that is a precursor, for example, alkoxysilanes or acyloxysilanes as mentioned above are used, the alkoxysilanes or acyloxysilanes may be partially hydrolyzed and condensed with an acid such as hydrochloric acid or sulfuric acid, a hydroxide of alkali metal or alkaline earth metal such as sodium hydroxide or potassium hydroxide, or an alkaline organic substance such as triethylamine as a reaction catalyst. When the partially (co)hydrolyzed condensates are directly produced from chlorosilanes, water and alcohol may be reacted with the chlorosilanes using by-product hydrochloric acid as a catalyst.

The silane coupling agents in the resin composition of the invention may be used individually, or may be used in combination of two or more types.

The content of the silane coupling agent (which may includes the (co)hydrolyzed condensate) contained in the composition 1 used in the invention is preferably in the range of 0.1 mass % to 80 mass %, more preferably in the range of 1 mass % to 40 mass %, and most preferably 5 mass % to 30 mass %, in terms of the solid content.

In the composition 1 of the invention, when a binder polymer having a hydroxyl group is used as the polymer, the silane coupling group of the silane coupling agent may undergo an alcohol exchange reaction with the hydroxyl group (—OH) in the polymer, and form a crosslinked structure. As a result, the molecules of the polymer are three-dimensionally crosslinked through the silane coupling agent.

The composition 1 of the invention preferably includes an alcohol exchange reaction catalyst in order to accelerate the formation of a crosslinked structure between the silane coupling agent and the polymer having a hydroxyl group.

Any alcohol exchange reaction catalyst may be applied without limitation, so long as it is a reaction catalyst that is generally used in silane coupling reactions. An acidic or basic catalyst, and a metal complex catalyst, which are representative alcohol exchange reaction catalysts, will be described in order.

(Acidic or Basic Catalyst)

In regard to the catalyst, an acidic or basic compound is used directly, or used in a state dissolved in a solvent such as water or an organic solvent (hereinafter, referred to as acidic catalyst and basic catalyst, respectively). The concentration in dissolving the catalyst in a solvent is not particularly limited, and may be appropriately selected in accordance with the characteristics of the acidic or basic compound in use, the desired content of the catalyst, or the like.

The type of the acidic catalyst or basic catalyst is not particularly limited, but specific examples of the acidic catalyst include hydrogen halide such as hydrochloric acid, nitric acid, sulfuric acid, sulfurous acid, hydrogen sulfide, perchloric acid, hydrogen peroxide, carbonic acid, a carboxylic acid such as formic acid or acetic acid, a substituted carboxylic acid in which R in the structural formula represented by RCOOH is substituted with another element or substituent, a sulfonic acid such as benzenesulfonic acid, phosphoric acid, and the like. Examples of the basic catalyst include an ammoniacal base such as ammonia water, an amine such as ethylamine or aniline, and the like. From the viewpoint of rapidly facilitating the alcohol exchange reaction in the film, the catalyst is preferably methanesulfonic acid, p-toluenesulfonic acid, pyridinium p-toluenesulfonate, phosphoric acid, phosphonic acid, or acetic acid, and is particularly preferably methanesulfonic acid, p-toluenesulfonic acid, or phosphoric acid.

(Metal Complex Catalyst)

The metal complex catalyst used as an alcohol exchange reaction catalyst in the invention preferably includes a metal element selected from Groups 2A, 3B, 4A and 5A of the Periodic Table, and an oxo or hydroxy oxygen compound selected from a β-diketone (acetylacetone or the like is preferable), a keto ester, a hydroxycarboxylic acid or an ester thereof, an aminoalcohol and an enolic active hydrogen compound.

Furthermore, among the constituent metal elements, Group 2A elements such as Mg, Ca, St and Ba, Group 3B elements such as Al and Ga, Group 4A elements such as Ti and Zr, and Group 5A elements such as V, Nb and Ta are preferable and form complexes with excellent catalytic effects. Among them, complexes obtainable from Zr, Al and Ti are excellent and preferable (ethyl orthotitanate, and the like).

These are excellent in the stability in aqueous coating liquids and the gelation accelerating effects in sol-gel reactions at the time of drying under heating, but among them, ethyl acetoacetate-aluminum diisopropionate, aluminum tris (ethyl acetoacetate), di(acetylacetonato)titanium complex salt, and zirconium tris(ethyl acetoacetate) are particularly preferable.

In the composition 1 of the invention, the alcohol exchange reaction catalysts may be used individually, or may be used in combination of two or more species. The content of the alcohol exchange reaction catalyst in the resin composition is preferably 0.01 to 20 mass %, and more preferably 0.1 to 10 mass %, based on the binder polymer having a hydroxyl group.

The total content of the (D) crosslinking agent, including the sulfur-containing polyfunctional monomer, in the composition 1 is preferably in the range of 10 mass % to 60 mass %, and more preferably 15 mass % to 45 mass %, based on the total solid content of the composition 1, from the viewpoint of flexibility or brittleness of the crosslinked film.

In the case of using the sulfur-containing polyfunctional monomer with another polymerizable compound in combination, the amount of the sulfur-containing polyfunctional monomer in the total polymerizable compounds in the composition 1 is preferably 5 mass % or more, and more preferably 10 mass % or more.

<Solvent>

The solvent that is used upon preparing the composition 1 of the invention is not particularly limited, but examples thereof include acetonitrile, tetrahydrofuran, dioxane, toluene, propylene glycol monomethyl ether acetate, methyl ethyl ketone, acetone, methyl isobutyl ketone, ethyl acetate, butyl acetate, ethyl lactate, N,N-dimethylacetamide, N-methylpyrrolidone, dimethylsulfoxide, methanol, ethanol, 1-propanol, 2-propanol, 1-butanol, 1-methoxy-2-propanol, ethylene glycol, diethylene glycol, and 1,3-propanediol.

When the composition 1 obtained as described above is crosslinked by heating, a composition for relief forming layer formation, which is composition 2, may be obtained. Here, in regard to the method of inducing crosslinking by heating, the composition 2 may be obtained by applying the composition 1 on a support as a relief forming layer, and directly or after drying the composition 1 at a temperature lower than the crosslinking temperature, heating the composition 1 at a temperature in the range of 50° C. to 150° C. for 0.5 hours to 24 hours to crosslink the composition 1.

When the (A) specific polymer is crosslinked, the specific polymer (when a polymerizable compound is used, the polymerizable compound is included) included in the composition 2 forms a three-dimensionally crosslinked structure. Accordingly, it is considered that when the relief forming layer is produced, physical properties of the relief layer obtained therefrom is enhanced, and the printing durability is improved even when printing pressure is repeatedly applied during printing over a long time.

Furthermore, when this (A) specific polymer has a linking group which has a sulfur atom bonded to carbon in the molecule, it is thought that since the binding energy is low, the polymer undergoes thermal decomposition more easily by laser engraving, and the engraving sensitivity is further enhanced.

As such, the molecules of the (A) specific polymer (when a crosslinking agent is used, the crosslinking agent is included) form a crosslinked structure at the time of the preparation of the composition and the formation of the film thereof, whereby various excellent properties are exhibited.

In the composition 2 used in the invention, formation of a crosslinked structure may be usually confirmed easily from the changes of film properties as described below.

The film after crosslinking may be identified using “solid $^{13}C$-NMR”.

The carbon atoms that are directly bonded to the unsaturated group in the (A) specific polymer undergo a change in the electronic environment before and after the polymerization reaction induced by heat, and thus concomitantly with this, undergo a change in the position of the peak. When the intensities of the carbon peak of the unsaturated group before and after crosslinking are compared, it may be known whether the polymerization reaction, which is the crosslinking reaction, is in progress, and the approximate ratio of the reaction. Here, since the degree of the change in the position of peak varies depending on the structure of the (A) specific polymer used, this change is a relative indicator.

Another method may be a method of immersing the film in a solvent before and after crosslinking, and observing the changes in the external appearance of the film by visual inspection. By this method, it is also possible to monitor the progress of crosslinking.

Specifically, the composition 2 is formed into a film, this composition film is immersed in acetone at room temperature for 24 hours, and the external appearance is observed by visual inspection. When a crosslinked structure has not been formed, or when a crosslinked structure has been slightly formed, the film dissolves in acetone to deform to the extent that the external appearance is not maintained, or the film dissolves to the extent that a solid object cannot be verified by visual inspection. However, when the film has a crosslinked structure, the film becomes insoluble, and the external appearance of the film is retained in the state before the immersion in acetone.

The composition 1 and composition 2 used in the invention may also include, in addition to the essential components of the (A) specific polymer, (B) carbon black and (C) thermopolymerization initiator, optional components such as (D) a crosslinking agent, (A-2) another polymer that may be used in combination, (B-2) another heat converting agent, plasticizer and the like according to the purpose, so long as these components do not impair the effect of the invention. Hereinafter, these components will be respectively described in detail.

<(A-2) Another Polymer that May be Used in Combination>

The composition 1 and composition 2 used in the invention may contain a known polymer that is not included in the (A) specific polymer, in combination with the (A) specific polymer. Hereinafter, such a polymer will be referred to as (A-2) another polymer that may be used in combination.

The (A-2) another polymer that may be used in combination constitutes, together with the (A) specific polymer, the main components contained in the composition for the relief forming layer, and a general polymer compound that is not included in the (A) specific polymer may be appropriately selected and used individually or in combination of two or more types. Particularly, when the resin composition for laser engraving is used in a printing plate precursor, it is necessary to select the polymer while taking into consideration various performances such as laser engraving properties, ink applicability and engraving waste dispersibility.

The another polymer that may be used in combination may be selected from a polystyrene resin, a polyester resin, a polysulfone resin, a polyether sulfone resin, a polycarbonate resin, an acrylic resin, an acetal resin, a polycarbonate resin, a rubber, a thermoplastic elastomer and the like, for use.

For example, from the viewpoint of laser engraving sensitivity, a polymer containing a partial structure that is thermally decomposed by light exposure or heating, is preferable. Preferable examples of such a polymer are described in paragraph [0038] of Japanese Patent Application Laid-Open (JP-A) No. 2008-163081. Furthermore, for example, when it is intended to form a film that is soft and has flexibility, a soft resin or a thermoplastic elastomer is selected. Examples thereof are described in detail in paragraphs [0039] to [0040] of Japanese Patent Application Laid-Open (JP-A) No. 2008-163081. When a resin composition for laser engraving is applied to a relief forming layer in a relief printing plate precursor for laser engraving, it is preferable to use a hydrophilic or alcoholphilic polymer, from the viewpoint of the ease of preparation of the composition for relief forming layer, and an enhancement of the resistance to oily inks in the resulting relief printing plate. Examples of the hydrophilic polymer that may be used are described in detail in paragraph [0041] of Japanese Patent Application Laid-Open (JP-A) No. 2008-163081.

A polyester formed from a hydroxycarboxylic acid unit, such as polylactic acid, may also be preferably used. Such a polyester is preferably selected from the group consisting of, specifically, a polyhydroxyalkanoate (PHA), a lactic acid-based polymer, polyglycolic acid (PGA), polycaprolactone (PCL), poly(butylenesuccinic acid), derivatives thereof, and mixtures thereof.

In addition, when the polymer is used for the purpose of curing by heating to enhance the strength, a polymer having a carbon-carbon unsaturated bond in the main chain is also preferably used.

Examples of the polymer containing a carbon-carbon unsaturated bond in the main chain include SB (polystyrene-polybutadiene), SBS (polystyrene-polybutadiene-polystyrene), SIS (polystyrene-poly isoprene-polystyrene), SEBS (polystyrene-polyethylene/polybutylene-polystyrene), and the like.

As such, binder polymers may be selected according to the purpose, while taking into consideration the properties in accordance with the applications of the relief printing plate, and the binder polymers may be used individually, or in combination of two or more polymers.

The total content of the polymer [sum of the contents of (A) specific polymer and (A-2) another polymer that may be used in combination] is preferably 5 mass % to 95 mass %, more preferably 15 mass % to 80 mass %, and even more preferably 20 mass % to 65 mass %, based on the total mass (solid content) of the composition for relief forming layer.

For example, when the composition for relief forming layer used in the invention is applied to a relief forming layer of a relief printing plate precursor, by adjusting the total content of the polymer to 5 mass % or more, a printing durability that is sufficient to use the resulting relief printing plate as a printing plate, is obtained. Further, by adjusting the total content to 80 mass % or less, there is no insufficiency in other components, and even when the relief printing plate is used as a flexo printing plate, a flexibility sufficient to be used as a printing plate may be obtained.

<(B-2) Photothermal Converting Agent Other than Carbon Black>

The relief forming layer according to the invention may further contain (B-2) a photothermal converting agent other than carbon black.

When the relief forming layer for laser engraving according to the invention is used in a laser engraving process of using a laser emitting infrared radiation having a wavelength of 700 nm to 1300 nm (YAG laser, semiconductor laser, fiber laser, surface emitting laser, or the like) as a light source, it is preferable to use a compound having the maximum absorption wavelength in the region of 700 nm to 1300 nm, as the photothermal converting agent.

Various dyes or pigments may be used as the photothermal converting agent according to the invention.

Among the (B-2) photothermal converting agents other than carbon black, examples of dyes that may be used include commercially available dyes and known dyes described in documents such as, for example, “Handbook of Dyes” (edited by the Society of Synthetic Organic Chemistry, Japan, published in 1970). Specifically, those having the maximum absorption wavelength in the region of 700 nm to 1300 nm may be exemplified, and dyes such as azo dyes, metal complex salt-azo dyes, pyrazolone azo dyes, naphthoquinone dyes, anthraquinone dyes, phthalocyanine dyes, carbonium dyes, diimmonium compounds, quinonimine dyes, methine dyes, cyanine dyes, squarylium colorants, pyrilium salts, and metal thiolate complexes may be exemplified. Particularly, cyanine dyes such as heptamethine cyanine dyes, oxonol dyes such as pentamethine oxonol dyes, and phthalocyanine dyes are preferably used, and for example, the dyes described in paragraphs [0124] to [0137] of Japanese Patent Application Laid-Open (JP-A) No. 2008-63554 may be exemplified.

Among the photothermal converting agents used in the invention, examples of pigments that may be used include commercially available pigments, and the pigments described in the Color Index (C.I.) Handbook, "Handbook of New Pigments" (edited by Japan Association of Pigment Technology, published in 1977), "New Pigment Application Technology" (published by CMC, Inc., in 1986), and "Printing Ink Technology" (published by CMC, Inc., in 1984).

Examples of the pigment include black pigments, yellow pigments, orange pigments, brown pigments, red pigments, violet pigments, blue pigments, green pigments, fluorescent pigments, metal powder pigments, and other polymer-bonded pigments. Specific examples include insoluble azo pigments, azo lake pigments, condensed azo pigments, chelate azo pigments, phthalocyanine pigments, anthraquinone pigments, perylene and perinone pigments, thio indigo pigments, quinacridone pigments, dioxazine pigments, isoindolinone pigments, quinophthalone pigments, dye lake pigments, azine pigments, nitroso pigments, nitro pigments, natural pigments, fluorescent pigments, inorganic pigments, and the like.

The content of the (B-2) photothermal converting agent other than carbon black in the total solid content of the relief forming layer may vary greatly depending on the magnitude of the molecular extinction coefficient inherent to the molecule, but is preferably in the range of 0.01 mass % to 20 mass %, more preferably in the range of 0.05 mass % to 10 mass %, and particularly preferably in the range of 0.1 mass % to 5 mass %.

<Additional Additives>

The composition for relief forming layer (composition 2) used in the invention preferably contains a plasticizer. The plasticizer has an action of softening the film formed by the composition for relief forming layer, and is required to have good compatibility with the polymer.

Examples of the plasticizer include dioctyl phthalate, didodecyl phthalate and the like, polyethylene glycols, polypropylene glycol (mono-ol type or diol type), and polypropylene glycol (mono-ol type or diol type) is preferably used.

The composition for the relief forming layer of the invention more preferably includes, as an additive for enhancing the engraving sensitivity, nitrocellulose or a high heat-conductive substance. Since nitrocellulose is a self-reactive compound, the compound itself generates heat upon laser engraving, and assists thermal decomposition of the co-present binder polymer such as a hydrophilic polymer. It is considered that the engraving sensitivity is enhanced as a result.

The high heat-conductive substance is added for the purpose of aiding in heat transfer, and examples of the heat-conductive substance include inorganic compounds such as metal particles, and organic compounds such as conductive polymers. The metal particles are preferably gold microparticles, silver microparticles and copper microparticles, which have a particle size in the order of micrometers to several nanometers. The conductive polymers are particularly preferably conjugated polymers, and specific examples include polyaniline and polythiophene.

The sensitivity at the time of photocuring the composition for relief forming layer may be further enhanced by using a co-sensitizer.

In order to inhibit any unnecessary thermal polymerization of the polymerizable compound during the production or storage of the composition, it is desirable to add a small amount of a thermopolymerization inhibiting agent.

A colorant such as a dye or a pigment may also be added for the purpose of coloring the composition for the relief forming layer. Thereby, properties such as the visibility of the image parts or the adaptability to the image density analyzer may be enhanced.

Furthermore, known additives such as fillers may also be added to improve the properties of a cured film of the composition for relief forming layer.

The relief printing plate precursor for laser engraving of the invention has a relief forming layer formed from a resin composition for relief forming layer containing the components as described above. The relief forming layer is preferably provided on a support.

According to the invention, the "relief printing plate precursor for laser engraving" means a relief printing plate precursor in which a crosslinkable relief forming layer formed of a resin composition for laser engraving has been cured by heat. When this printing plate precursor is laser engraved, a "relief printing plate" is produced.

If necessary, the relief printing plate precursor for laser engraving may further have an adhesive layer between the support and the relief forming layer, and a slip coat layer and a protective film on the relief forming layer.

<Relief Forming Layer>

The relief forming layer is a layer formed from the composition for laser engraving of the invention. When a crosslinkable composition is used as the composition for laser engraving, a crosslinkable relief forming layer is obtained. It is preferable that the relief printing plate precursor for laser engraving of the invention has a relief forming layer that is formed by thermally crosslinking a composition 1 prepared by further imparting a function of crosslinkability by further incorporating the (D) crosslinking agent into a resin composition containing the (A) polymer having an ethylenically unsaturated bond in a side chain, (B) carbon black, and (C) thermopolymerization initiator.

According to an embodiment of producing a relief printing plate from a relief printing plate precursor for laser engraving, it is preferable that a relief forming layer be cured by thermally crosslinking to obtain a relief printing plate precursor having a cured relief forming layer, and the cured relief forming layer (hard relief forming layer) is laser-engraved to thereby form a relief layer, and to thus produce a relief printing plate. Since the relief forming layer is crosslinked, abrasion of the relief layer during printing may be prevented, and a relief printing plate having a relief layer which acquires a sharp shape after laser engraving may be obtained.

The relief forming layer may be formed by molding the resin composition for laser engraving having the components as described above for relief forming layer into a sheet shape or sleeve shape.

<Support>

A support that may be used for relief printing plate precursor for laser engraving will be described.

The material used in the support for the relief printing plate precursor for laser engraving is not particularly limited, but a material having high dimensional stability is preferably used. Examples include metals such as steel, stainless steel and aluminum, plastic resins such as polyester (for example, PET, PBT, PAN) or polyvinyl chloride, synthetic rubbers such as styrene-butadiene rubber, and plastic resins (epoxy resin, phenolic resin and the like) reinforced with glass fiber. As for the support, a PET (polyethylene terephthalate) film or a steel substrate is preferably used. The shape of the support is determined by whether the relief forming layer has a sheet shape or a sleeve shape. In regard to a relief printing plate precursor for laser engraving that has been produced by coating a crosslinkable resin composition for laser engraving, and curing the resin composition from the rear surface (refers to the surface opposite to the surface where laser engraving is performed, and also includes a cylindrically shaped surface) by light, heat or the like, since the rear surface side of the cured resin composition for laser engraving may function as a support, the support is not necessarily essential.

<Adhesive Layer>

An adhesive layer may be provided between the relief forming layer and the support, for the purpose of reinforcing the adhesive power between the two layers. Examples of the material (adhesive) that may be used in the adhesive layer include those described in I. Skeist, ed., "Handbook of Adhesives", $2^{nd}$ edition (1977).

<Protective Film, Slip Coat Layer>

For the purpose of preventing scratches or depression at the surface of the relief forming layer, a protective film may be provided on the surface of the relief forming layer. The thickness of the protective film is preferably 25 μm to 500 μm, and more preferably 50 μm to 200 μm. Examples of the protective film that may be used include polyester films such as PET (polyethylene terephthalate), and polyolefin films such as PE (polyethylene) or PP (polypropylene). Furthermore, the surface of the film may be matted. In the case of providing a protective film on the relief forming layer, the protective film should be peelable.

When the protective film is unpeelable, or on the other hand, when it is difficult to adhere the protective film to the relief forming layer, a slip coat layer may be provided between the two layers. It is preferable that the material used in the slip coat layer contain a resin that is soluble or dispersible in water and is less adhesive, such as polyvinyl alcohol, polyvinyl acetate, partially saponified polyvinyl alcohol, hydroxyalkyl cellulose, alkyl cellulose or a polyamide resin, as a main component.

—Method for Producing Relief Printing Plate Precursor for Laser Engraving—

Next, the method for producing a relief printing plate precursor for laser engraving will be described.

The formation of a relief forming layer in a relief printing plate precursor for laser engraving is not particularly limited, but for example, a method of preparing a composition for the relief forming layer (containing a composition for laser engraving), removing the solvent from this composition for relief forming layer, and then melt extruding the composition on a support, may be exemplified. Alternatively, a method of flow casting the composition for relief forming layer on a support, drying this in an oven, and removing the solvent from the composition, may also be used.

Subsequently, a protective film may also be laminated on a relief forming layer, if necessary. The lamination may be performed by pressing a protective film and a relief forming layer with a heated calendar roll, or by adhering a protective film on a relief forming layer impregnated with a small amount of solvent on the surface.

In the case of using a protective film, a method of first laminating a relief forming layer on the protective film, and then laminating a support thereon, may also be employed.

In the case of providing an adhesive layer, this may be handled by using a support having an adhesive layer coated thereon. In the case of providing a slip coat layer, this may be handled by using a protective film having a slip coat layer coated thereon.

The composition for relief forming layer (composition 2) may be prepared by, for example, dissolving the (A) specific polymer, (B) carbon black and the like in an appropriate solvent, subsequently dissolving the (C) thermopolymerization initiator, and optional components such as (D) a crosslinking agent and the like, and heating the solution in the temperature range mentioned above. Since most of the solvent component needs to be removed at the stage of producing the relief printing plate precursor, it is preferable to use easily evaporable low molecular alcohols (for example, methanol, ethanol, n-propanol, isopropanol, propylene glycol monomethyl ether) and the like as the solvent, and to suppress the total amount of addition of the solvent to be as small as possible by adjusting the temperature or the like.

Here, according to the invention, the term "relief printing plate precursor for laser engraving" refers to the state in which a relief forming layer has been crosslinked, as described above. For the method of crosslinking the relief forming layer, it is preferable to carry out a step of crosslinking the relief forming layer by heating (step (1) in the method for producing a relief printing plate of the invention that will be described later).

The thickness of the relief forming layer in the relief printing plate precursor for laser engraving is preferably 0.05 mm or more and 10 mm or less, more preferably 0.05 mm or more and 7 mm or less, and particularly preferably 0.05 mm or more and 3 mm or less, with respect to before and after crosslinking.

[Relief Printing Plate and Production Thereof]

The method for producing a relief printing plate using the relief printing plate precursor of the invention includes (1) a step of heating the relief forming layer in the relief printing plate precursor for laser engraving of the invention to crosslink the layer (hereinafter, appropriately referred to as "step (1)"), and (2) a step of laser engraving the crosslinked relief forming layer to form a relief layer (hereinafter, appropriately referred to as "step (2)").

With the method for producing a relief printing plate using the relief printing plate precursor of the invention, the relief printing plate of the invention having a relief layer on a support may be produced.

<Step (1)>

The relief printing plate precursor for laser engraving of the invention has a relief forming layer in a state cured by crosslinking, as described above. In order to obtain such a relief forming layer, it is preferable to use a step of crosslinking the relief forming layer in the relief printing plate precursor for laser engraving of the invention by heating.

Examples of heating technique include a method of heating the printing plate precursor in a hot air oven or far-infrared oven for a predetermined time, or a method of contacting the printing plate precursor with a heated roll for a predetermined time.

Since the relief forming layer is crosslinked, there are advantages such as that, firstly, the relief formed after laser engraving becomes sharp, and secondly, the adhesiveness of the engraving waste generated at the time of laser engraving is suppressed.

<Step (2)>

In the method for producing a relief printing plate of the invention, (2) a step of forming a relief layer by laser engraving the crosslinked relief forming layer is carried out after the step (1) described above. With the method for producing a relief printing plate of the invention, the relief printing plate of the invention having a relief layer on a support may be produced.

The step (2) is a step of forming a relief layer by laser engraving the relief forming layer crosslinked in the step (1). Specifically, the relief layer is formed by performing engraving by irradiating the crosslinked relief forming layer with a laser light corresponding to the image that is intended to be formed. Preferably, there may be exemplified a step of scan irradiating the relief forming layer by controlling the laser head with a computer based on the digital data of the image that is intended to be formed.

In this step (2), an infrared laser is preferably used. When an infrared laser light is irradiated, the molecules in the relief forming layer start molecular vibration, and thus heat is generated. When a high output power laser such as a carbon dioxide laser or a YAG laser is used as the infrared laser, a large amount of heat is generated at the laser-irradiated part, and the molecules in the relief forming layer undergo molecular cleavage or ionization, and selective removal, that is, engraving, is achieved. The advantage of laser engraving is that because the engraving depth may be arbitrarily set, the structure may be three-dimensionally controlled. For example, the parts for printing fine halftone dots may be made such that the relief does not fall down due to printing pressure, by performing shallow engraving or shouldered engraving. The groove parts for printing fine outline characters may be made such that it is difficult for the ink to fill in the grooves, and the outline characters are prevented from collapsing, by engraving deeply.

Particularly, in the case of performing engraving with an infrared laser corresponding to the absorption wavelength of the photothermal converting agent, selective removal of the relief forming layer with higher sensitivity is made possible, and a relief layer having a sharp image may be obtained. The infrared laser used in a step (2) is preferably a carbon dioxide laser or a semiconductor laser, from the viewpoints of productivity, costs and the like. Particularly, a fiber-coupled semiconductor infrared laser is preferably used. In general, semiconductor lasers have higher laser oscillation efficiency compared to $CO_2$ lasers, and the cost is low and the size reduction may be achieved. In addition, since the semiconductor laser is small in size, arraying is easily achieved. The beam shape may be controlled by fiber treatment. In regard to the semiconductor laser, a laser having a maximum absorption wavelength of 700 nm to 1300 nm may be used, but a laser having a maximum absorption wavelength of preferably 800 nm to 1200 nm, more preferably 860 nm to 1200 nm, and particularly preferably 900 nm to 1100 nm, may be used.

The method for producing a relief printing plate of the invention may further include the following step (3) to step (5), if necessary, subsequently to the step (2).

Step (3): A step of rinsing the engraved surface of the relief layer after engraving, with water or a liquid containing water as a main component (rinsing step).

Step (4): A step of drying the engraved relief layer (drying step).

Step (5): A step of further crosslinking the relief layer by applying energy to the relief layer after engraving (post-crosslinking step).

When engraving waste is attached to the engraved surface, the step (3) of rinsing the engraved surface with water or a liquid containing water as a main component to wash away the engraving waste, may also be added. As the rinsing technique, there may be exemplified a method of washing with tap water; a method of jet spraying high pressure water; a method of brush scrubbing the engraved surface mainly in the presence of water, with a brush type washout machine of a batch type or conveyor type known as a developing machine for photosensitive resin anastatic plates; and the like. If the slime of the engraving waste cannot be removed, a rinsing liquid containing a surfactant may also be used.

When the step (3) of rinsing the engraved surface is carried out, it is preferable to add the step (4) of drying the engraved relief forming layer to volatilize the rinsing liquid.

Furthermore, if necessary, the step (5) of further crosslinking the relief forming layer may also be added. By carrying out the additional crosslinking step (5), the relief formed by engraving may be made stronger and firmer.

As such, the relief printing plate of the invention having a relief layer on a support is obtained.

The thickness of the relief layer included in the relief printing plate is preferably 0.05 mm or greater and 10 mm or smaller, more preferably 0.05 mm or greater and 7 mm or smaller, and particularly preferably 0.05 mm or greater and 3 mm or smaller, from the viewpoint of satisfying various adaptabilities to flexo printing such as abrasion resistance or ink transferability.

Furthermore, the Shore A hardness of the relief layer included in the relief printing, plate is preferably 50° or greater and 90° or smaller.

When the Shore A hardness of the relief layer is 50° or greater, the fine halftone dots formed by engraving do not collapse and break down even under the high printing pressure of an anastatic printing machine, and normal printing may be achieved. Further, when the Shore A hardness of the relief layer is 90° or smaller, printing fading at solid image parts may be prevented even in flexo printing, where the printing pressure is kiss-touch pressure.

Here, the Shore A hardness in the specification is a value measured by a durometer (spring type rubber hardness meter), which presses an indenter (also called an indenting needle) on the surface of an object of measurement to cause a deformation, measures the amount of deformation (indent depth), and converts the measurement into numeral data.

The relief printing plate produced by the production method of the invention allows printing by an anastatic printing machine using an oily ink or a UV ink, and printing by a flexo printing machine using a UV ink is also possible.

According to the invention, for example, the following embodiments <1> to <9> may be provided.

<1> A relief printing plate precursor for laser engraving, comprising a relief forming layer formed by thermally crosslinking a resin composition comprising (A) a polymer having an ethylenically unsaturated bond in a side chain wherein the polymer is an acrylic resin or a polyvinyl acetal, (B) carbon black, and (C) a thermopolymerization initiator.

<2> The relief printing plate precursor for laser engraving according to <1>, wherein the (A) polymer having an ethylenically unsaturated bond in a side chain is a polyvinyl acetal.

<3> The relief printing plate precursor for laser engraving according to <1> or <2>, wherein the (A) polymer having an ethylenically unsaturated bond in a side chain is a polymer having a carbon-heteroatom bond between the main chain and the ethylenically unsaturated bond in a side chain.

<4> The relief printing plate precursor for laser engraving according to <3>, wherein the (A) polymer having an ethylenically unsaturated bond in a side chain is a polymer having a carbon-sulfur bond between the main chain and the ethylenically unsaturated bond in a side chain.

<5> The relief printing plate precursor for laser engraving according to any one of <1> to <4>, wherein the glass transition temperature of the (A) polymer having an ethylenically unsaturated bond in a side chain is from 20° C. to 200° C.

<6> The relief printing plate precursor for laser engraving according to any one of <1> to <5>, wherein the resin composition further comprises (D) a crosslinking agent.

<7> The relief printing plate precursor for laser engraving according to <6>, wherein the (D) crosslinking agent is a compound having an ethylenically unsaturated bond.

<8> A method for producing a relief printing plate, comprising forming a relief layer by subjecting the relief forming layer in the relief printing plate precursor for laser engraving according to any one of <1> to <7> to laser engraving.

<9> The method for producing a relief printing plate according to <8>, wherein the laser engraving is laser engraving using as a light source a semiconductor laser including a plurality of fibers and having a wavelength of 700 nm to 1200 nm.

Therefore, according to the invention, a relief printing plate precursor for laser engraving, which has excellent printing durability and has high engraving sensitivity when subjected to laser engraving, may be provided.

Furthermore, a method for producing a relief printing plate using the relief printing plate precursor may be provided.

EXAMPLES

Hereinafter, the invention will be described in more detail based on Examples, but the invention is not intended to be limited to these Examples. The weight average molecular weight (Mw) of a polymer in the Examples indicates, unless stated otherwise, a value measured by a GPC method.

(Synthesis of P-1)

A three-necked flask equipped with a stirring blade and a cooling tube was charged with DENKA BUTYRAL #3000-2 (manufactured by Denki Kagaku Kogyo Co., Ltd., polyvinyl butyral, Mw=90000, 100 g), pyridine (manufactured by Wako Pure Chemical Industries, Ltd., 7.91 g), and 4-hydroxy-2,2,6,6-tetramethylpyridin-1-oxyl free radical (manufactured by Tokyo Chemical Industry Co., Ltd., 0.20 g), and the mixture was dissolved in tetrahydrofuran (manufactured by Wako Pure Chemical Industry, Ltd., 1000 g). This solution was cooled in an ice bath, and acrylic acid chloride (manufactured by Tokyo Chemical Industry Co., Ltd., 9.05 g) was added dropwise thereto over one hour. The ice bath was removed, and the mixture was further stirred for 3 hours at room temperature. Then, this solution was poured into water (10 L). A precipitated solid was collected by filtration, rinsed with water, and then air-dried, to obtain P-1 (105 g). The structure of the obtained P-1 was identified by $^{1}$H-NMR.

(Synthesis of P-2)

P-2 was synthesized in the same manner as in the synthesis of P-1, except that acrylic acid chloride used in the synthesis of P-1 was changed to methacrylic acid chloride (manufactured by Tokyo Chemical Industry Co., Ltd.). The structure of the obtained P-2 was identified by $^{1}$H-NMR.

(Synthesis of P-3)

A three-necked flask equipped with a stirring blade and a cooling tube was charged with DENKA BUTYRAL #3000-2 (manufactured by Denki Kagaku Kogyo Co., Ltd., polyvinyl butyral, Mw=90,000, 100 g), di-n-butyltin dilaurate (manufactured by Wako Pure Chemical Industries, Ltd., 0.10 g), and 4-hydroxy-2,2,6,6-tetramethylpyridin-1-oxyl free radical (manufactured by Tokyo Chemical Industry Co., Ltd., 0.20 g), and the mixture was dissolved in tetrahydrofuran (manufactured by Wako Pure Chemical Industries, Ltd., 1000 g). KARENZ MOI (manufactured by Showa Denko K.K., 15.51 g) was added dropwise to the solution over one hour. The mixture was further stirred for 6 hours at room temperature, and then this solution was poured into water (10 L). A precipitated solid was collected by filtration, rinsed with water, and then air-dried, to obtain P-3 (110 g). The structure of the obtained P-3 was identified by $^{1}$H-NMR.

(Synthesis of P-4)

P-4 was synthesized in the same manner as in the synthesis of P-3, except that KARENZ MOI used in the synthesis of P-3 was changed to KARENZ BEI (manufactured by Showa Denko K.K.). The structure of the obtained P-4 was identified by $^{1}$H-NMR.

(Synthesis of P-5)

A three-necked flask equipped with a stirring blade and a cooling tube was charged with DENKA BUTYRAL #3000-2 (manufactured by Denki Kagaku Kogyo Co., Ltd., polyvinyl butyral, Mw=90,000, 100 g), 3-(trimethoxysilyl)propyl methacrylate (manufactured by Tokyo Chemical Industry Co., Ltd., 24.84 g), and 4-hydroxy-2,2,6,6-tetramethylpyridin-1-oxyl free radical (manufactured by Tokyo Chemical Industry Co., Ltd., 0.20 g), and the mixture was dissolved in methyl ethyl ketone (manufactured by Wako Pure Chemical Industries, Ltd., 1000 g). Triethylamine (manufactured by Kanto Chemical Co., Inc., 0.35 g) was added, and the mixture was stirred for 3 hours at 70° C. The mixture was cooled to room temperature, and then the solvent was distilled off, to obtain P-5 (120 g). The structure of the obtained P-5 was identified by $^{1}$H-NMR.

(Synthesis of P-6)

A three-necked flask equipped with a stirring blade and a cooling tube was charged with DENKA BUTYRAL #3000-2 (manufactured by Denki Kagaku Kogyo Co., Ltd., polyvinyl butyral, Mw=90,000, 100 g) and 1-ethyl-3-(3-dimethylaminopropyl)carbodiimide hydrochloride (manufactured by Tokyo Chemical Industry Co., Ltd., 82.43 g), and the mixture was dissolved in 1000 g of acetone. This solution was cooled in an ice bath, and thioglycolic acid (manufactured by Tokyo Chemical Industry Co., Ltd., 39.61 g) was added dropwise thereto over one hour. The ice bath was removed, the mixture was further stirred for 3 hours at room temperature, and then this solution was poured into water (10 L). A precipitated solid was collected by filtration, rinsed with water, and then air-dried, to obtain P-6' (130 g).

A three-necked flask equipped with a stirring blade and a cooling tube was charged with P-6' (100 g), pyridine (manufactured by Wako Pure Chemical Industries, Ltd., 20.00 g) and 4-hydroxy-2,2,6,6-tetramethylpyridin-1-oxyl free radical (manufactured by Tokyo Chemical Industry Co., Ltd., 0.20 g), and the mixture was dissolved in tetrahydrofuran (manufactured by Wako Pure Chemical Industries, Ltd., 1000 g). This solution was cooled in an ice bath, and methacrylic acid chloride (manufactured by Tokyo Chemical Industry Co., Ltd., 26.44 g) was added dropwise thereto over one hour. The ice bath was removed, and the mixture was further stirred for 3 hours at room temperature. Then, this solution was poured into water (10 L). A precipitated solid was collected by filtration, rinsed with water, and then air-dried, to obtain P-6 (130 g). The structure of the obtained P-6 was identified by $^{1}$H-NMR.

(Synthesis of P-7)

P-7 was synthesized in the same manner as in the synthesis of P-6, except that methacrylic acid chloride used in the synthesis of P-6 was changed to acrylic acid chloride (manufactured by Tokyo Chemical Industry Co., Ltd.). The structure of the obtained P-7 was identified by $^{1}$H-NMR.

(Synthesis of P-8)

A three-necked flask equipped with a stirring blade and a cooling tube was charged with P-6' (100 g), V-65 (manufactured by Wako Pure Chemical Industries, Ltd., 0.25 g) and acrylic acid (manufactured by Wako Pure Chemical Industries, Ltd., 7.21 g), and the mixture was dissolved in tetrahydrofuran (manufactured by Wako Pure Chemical Industries, Ltd., 1000 g). This solution was stirred for 5 hours at 70° C. under a nitrogen atmosphere. To this solution, glycidyl methacrylate (manufactured by Wako Pure Chemical Industries, Ltd., 14.21 g), tetraethylammonium bromide (manufactured by Wako Pure Chemical Industries, Ltd., 0.21 g) and 4-hydroxy-2,2,6,6-tetramethylpyridin-1-oxyl free radical (manufactured by Tokyo Chemical Industry Co., Ltd., 0.20 g) were added, and the mixture was further stirred for 5 hours at 60° C. This solution was cooled to room temperature, and was poured into water (10 L). A precipitated solid was collected by filtration, rinsed with water, and then air-dried, to obtain P-8 (110 g). The structure of the obtained P-8 was identified by $^1$H-NMR.

(Synthesis of P-9)

A three-necked flask equipped with a stirring blade and a cooling tube was charged with P-6' (100 g), V-65 (manufactured by Wako Pure Chemical Industries, Ltd., 0.25 g) and (2-hydroxyethyl) acrylate (manufactured by Tokyo Chemical Industry Co., Ltd., 11.61 g), and the mixture was dissolved in tetrahydrofuran (manufactured by Wako Pure Chemical Industries, Ltd., 1000 g). This solution was stirred for 5 hours at 60° C., and then stirred for one hour at 70° C. To this solution, 1-ethyl-3-(3-dimethylaminopropyl)carbodiimide hydrochloride (manufactured by Tokyo Chemical Industry Co., Ltd., 19.16 g) was added. This solution was cooled in an ice bath, and methacrylic acid (manufactured by Wako Pure Chemical Industries, Ltd., 8.61 g) was added dropwise over one hour. The ice bath was removed, the solution was further stirred for 3 hours at room temperature, and this solution was poured into water (10 L). A precipitate solid was collected by filtration, rinsed with water, and then air-dried, to obtain P-9 (100 g). The structure of the obtained P-9 was identified by $^1$H-NMR.

(Synthesis of P-10)

A three-necked flask equipped with a stirring blade and a cooling tube was charged with P-6' (100 g), di-n-butyltin dilaurate (manufactured by Wako Pure Chemical Industries, Ltd., 0.16 g) and 4-hydroxy-2,2,6,6-tetramethylpyridin-1-oxyl free radical (manufactured by Tokyo Chemical Industry Co., Ltd., 0.20 g), and the mixture was dissolved in tetrahydrofuran (manufactured by Wako Pure Chemical Industries, Ltd., 1000 g). KARENZ MOI (manufactured by Showa Denko K.K., 15.51 g) was added dropwise to this solution over one hour. The mixture was further stirred for 6 hours at room temperature, and then this solution was poured into water (10 L). A precipitated solid was collected by filtration, rinsed with water, and then air-dried, to obtain P-10 (110 g). The structure of the obtained P-10 was identified by $^1$H-NMR.

(Synthesis of P-11)

P-11 was synthesized in the same manner as in the synthesis of P-10, except that KARENZ MOI used in the synthesis of P-10 was changed to KARENZ BEI (manufactured by Showa Denko K.K.). The structure of the obtained P-11 was identified by $^1$H-NMR.

(Synthesis of P-12)

A three-necked flask equipped with a stirring blade and a cooling tube was charged with P-6' (100 g), triethylamine (manufactured by Kanto Chemical Co., Inc., 10.12 g) and 4-hydroxy-2,2,6,6-tetramethylpyridin-1-oxyl free radical (manufactured by Tokyo Chemical Industry Co., Ltd., 0.20 g), and the mixture was dissolved in tetrahydrofuran (manufactured by Wako Pure Chemical Industries, Ltd., 1000 g). Chloromethylstyrene CMS-14 (manufactured by Seimi Chemical Co., Ltd., 15.26 g) was added to this solution, the mixture was stirred for 6 hours at 70° C., and this solution was poured into water (10 L). A precipitated solid was collected by filtration, rinsed with water, and then air-dried, to obtain P-12 (110 g). The structure of the obtained P-12 was identified by $^1$H-NMR.

(Synthesis of P-13)

A three-necked flask equipped with a stirring blade and a cooling tube was charged with tetrahydrofuran (500 g), and this was stirred at 70° C. To this, a solution of methacrylic acid (manufactured by Wako Pure Chemical Industries, Ltd., 20.00 g), dicyclopentanyl methacrylate (manufactured by Tokyo Chemical Industry, Co., Ltd., 204.73 g), V-601 (manufactured by Wako Pure Chemical Industries, Ltd., 1.34 g) and tetrahydrofuran (500 g), was added dropwise over 3 hours. After completion of the dropwise addition, the mixture was further stirred for 3 hours at 70° C., and then this solution was poured into water (10 L). A precipitated solid was collected by filtration, rinsed with water, and then air-dried, to obtain P-13' (210 g).

A three-necked flask equipped with a stirring blade and a cooling tube was charged with P-13' (100 g), tetraethylammonium bromide (manufactured by Tokyo Chemical Industry Co., Ltd., 0.21 g) and 4-hydroxy-2,2,6,6-tetramethylpyridin-1-oxyl free radical (manufactured by Tokyo Chemical Industry Co., Ltd., 0.20 g), and the mixture was dissolved in tetrahydrofuran (1000 g). Glycidyl methacrylate (manufactured by Wako Pure Chemical Industries, Ltd., 14.21 g) was added to this solution, and then the mixture was stirred for 5 hours at 60° C. This solution was cooled to room temperature, and then poured into water (10 L). A precipitated solid was collected by filtration, rinsed with water, and then air-dried, to obtain P-13 (110 g). The structure of the obtained P-13 was identified by $^1$H-NMR.

(Synthesis of P-14)

A three-necked flask equipped with a stirring blade and a cooling tube was charged with P-13' (100 g), (2-hydroxyethyl)methacrylate (manufactured by Tokyo Chemical Industry Co., Ltd., 13.01 g) and 4-hydroxy-2,2,6,6-tetramethylpyridin-1-oxyl free radical (manufactured by Tokyo Chemical Industry Co., Ltd., 0.20 g), and the mixture was dissolved in tetrahydrofuran (1000 g). This solution was cooled in an ice bath, and a solution of 1-ethyl-3-(3-dimethylaminopropyl) carbodiimide hydrochloride (manufactured by Tokyo Chemical Industry Co., Ltd., 19.16 g) and tetrahydrofuran (100 g) was added dropwise thereto over one hour. The ice bath was removed, the mixture was further stirred for 3 hours at room temperature, and then this solution was poured into water (10 L). A precipitated solid was collected by filtration, rinsed with water, and then air-dried, to obtain P-14 (110 g). The structure of the obtained P-14 was identified by $^1$H-NMR.

(Synthesis of P-15)

A three-necked flask equipped with a stirring blade and a cooling tube was charged with tetrahydrofuran (500 g), and this was stirred at 70° C. To this, a solution of (2-hydroxyethyl)methacrylate (manufactured by Tokyo Chemical Industry, Co., Ltd., 20.00 g), dicyclopentanyl methacrylate (manufactured by Tokyo Chemical Industry, Co., Ltd., 135.43 g), V-601 (manufactured by Wako Pure Chemical Industries, Ltd., 1.34 g) and tetrahydrofuran (500 g), was added dropwise over 3 hours. After completion of the dropwise addition, the mixture was further stirred for 3 hours at 70° C., and was cooled in an ice bath. Pyridine (manufactured by Wako Pure Chemical Industries, Ltd., 12.26 g) and 4-hydroxy-2,2,6,6-tetramethylpyridin-1-oxyl free radical (manufactured by Tokyo Chemical Industry Co., Ltd., 0.31 g) were added to the mixture. Methacrylic acid chloride (manufactured by Tokyo Chemical Industry Co., Ltd., 16.20 g) was added dropwise to this solution over one hour. The ice bath was removed, and this solution was further stirred for 3 hours at room temperature and then was poured into water (10 L). A precipitated solid was collected by filtration, rinsed with water, and then air-dried, to obtain P-15 (150 g). The structure of the obtained P-15 was identified by $^1$H-NMR.

(Synthesis of P-16)

P-16 was synthesized in the same manner as in the synthesis of P-13, except that dicyclopentanyl methacrylate used in the synthesis of P-13 was changed to hexyl methacrylate. The structure of the obtained P-16 was identified by $^1$H-NMR.

(Synthesis of P-17)

P-17 was synthesized in the same manner as in the synthesis of P-15, except that dicyclopentanyl methacrylate used in the synthesis of P-15 was changed to hexyl methacrylate. The structure of the obtained P-17 was identified by $^1$H-NMR.

Example 1

1. Preparation of Composition for Relief Forming Layer for Laser Engraving

A three-necked flask equipped with a stirrer and a cooling tube was charged with 50 g of P-1 as a polymer and 47 g of propylene glycol monomethyl ether acetate as a solvent, and the polymer was dissolved by heating at 40° C. for 120 minutes under stirring. Subsequently, 15 g of a monomer (M-1: structure shown below) as the (D) crosslinking agent, 8 g of BLENMER-LMA (manufactured by Nippon Oil & Fats Co., Ltd.) as a crosslinking agent (monofunctional compound), 1.6 g of PERBUTYL Z (manufactured by Nippon Oil & Fats Co., Ltd.) as the (C) polymerization initiator, and 1 g of KETJENBLACK EC600JD (manufactured by Lion Corp.) as the (B) carbon black were further added to the solution, and the resultant was stirred for 30 minutes. A composition 1 for a relief forming layer having fluidity was obtained through this operation.

M-1

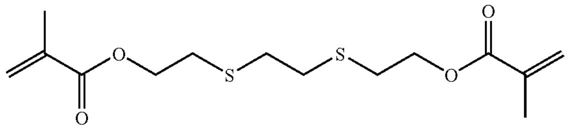

2. Production of Relief Printing Plate Precursor for Laser Engraving

A spacer (frame) having a predetermined thickness was provided on a PET substrate, and the crosslinkable composition 1 for relief forming layer obtained as described above was gently flow casted to the extent that the composition did not flow out over the spacer (frame). The composition was dried for 3 hours in an oven at 70° C. to provide a relief forming layer having a thickness of approximately 1 mm, and thus a relief printing plate precursor 1 for laser engraving was produced.

3. Production of Relief Printing Plate

The relief forming layer of the resulting relief printing plate precursor 1 for laser engraving was heated for 3 hours at 80° C. and for another 3 hours at 100° C. to thermally crosslink the relief forming layer.

The relief forming layer after crosslinking was subjected to engraving with the following two types of lasers.

Engraving by laser irradiation with a carbon dioxide laser engraving machine was performed using a high definition $CO_2$ LASER MARKER ML-9100 series (manufactured by Keyence Corp.). The protective film was peeled off from the printing plate precursor 1 for laser engraving, and then raster engraving was performed on a 1 cm-square solid image part with the carbon dioxide laser engraving machine under the conditions of an output power of 12 W, a head speed of 200 mm/second, and a pitch setup of 2400 DPI.

A laser recording apparatus equipped with a fiber-coupled semiconductor laser (FC-LD) SDL-6390 (manufactured by JDSU Corp., wavelength: 915 nm) having a maximum output power of 8.0 W was used as a semiconductor laser engraving machine. Raster engraving was performed on a 1 cm-square solid image part with the semiconductor laser engraving machine under the conditions of an output power of 7.5 W, a head speed of 409 mm/second, and a pitch setup of 2400 DPI.

The thickness of the relief layer included in the relief printing plate was approximately 1 mm.

Examples 2 to 19, Comparative Examples 1 to 4

Compositions for the relief forming layer of Examples 2 to 19 and Comparative Examples 1 to 3 were prepared in the same manner as in Example 1, except that the (A) specific polymer used in Example 1 was changed to the (A) specific polymer or comparative polymer indicated in the following Table 2. Furthermore, in Comparative Example 4, the composition for relief forming layer was prepared without using the carbon black used in example 1, as indicated in the following Table 2. Relief printing plates of Examples 2 to 19 and Comparative Examples 1 to 4 were obtained in the same manner as in Example 1, using these compositions. The thickness of the relief layers included in these relief printing plates was approximately 1 mm.

P-1 to P-19 used in Table 2 are exemplary compounds illustrated previously, and the polymers used in the Comparative Examples are as shown below.

#3000-2: Butyral resin manufactured by Denki Kagaku Kogyo Co., Ltd., weight average molecular weight 90000

TR2000: Styrene-butadiene copolymer manufactured by JSR Corp., weight average molecular weight 100000

Polyurethane: Polyurethane (Mw=90,000) obtained from tolylene diisocyanate/polypropylene glycol (Mw=2000) at a mass ratio of 50/50

5. Evaluation of Relief Printing Plate

A performance evaluation of the relief printing plate was performed on the following items, and the results are presented in Table 2.

5-1. Printing Durability

The obtained relief printing plate was mounted on a printing machine (ITM-4 type, manufactured by Iyo Kikai Seisakusho Co., Ltd.), and an aqueous ink AQUA SPZ16 RED (Toyo Ink Manufacturing Co., Ltd.) was used as the ink without diluting. Printing was continued using FULL COLOR FORM M70 (manufactured by Nippon Paper Group, thickness 100 μm) as a printing paper, and highlight 1 to 10% was checked on the printed matter. The time when unprinted halftone dots occurred was regarded as completion of printing, and the length (meter) of paper printed until the completion of printing was taken as the index. A larger value indicates excellent printing durability.

5-2. Engraving Depth

The "engraving depth" of a relief layer obtained by laser engraving the obtained relief printing plate was measured as follows. Here, the "engraving depth" means the difference between the position (height) of an engraved site and the position (height) of a non-engraved site, when the cross-section of the relief layer was observed. The "engraving depth" in the present Examples was measured by observing the cross-section of the relief layer with an ultra-deep color 3D profile measuring microscope, VK9510 (manufactured by Keyence Corp.). A larger engraving depth means higher engraving sensitivity. The results are presented in Table 2 for each type of laser used in the engraving.

TABLE 2

| | (A) Polymer | | | | | Evaluation results | | |
|---|---|---|---|---|---|---|---|---|
| | Compd | Main chain structure | Presence or absence of S atom | Presence or absence of carbon black | Crosslinking agent | Printing durability (m) | Engraving depth (μm) FC-LD | Engraving depth (μm) $CO_2$ laser |
| Ex. 1 | P-1 | PVB | Absent | Present | M-1 | 2000 | 395 | 316 |
| Ex. 2 | P-2 | PVB | Absent | Present | M-1 | 1800 | 400 | 322 |
| Ex. 3 | P-3 | PVB | Absent | Present | M-1 | 2100 | 405 | 326 |
| Ex. 4 | P-4 | PVB | Absent | Present | M-1 | 2300 | 400 | 322 |
| Ex. 5 | P-5 | PVB | Absent | Present | M-1 | 2000 | 400 | 322 |
| Ex. 6 | P-6 | PVB | Present | Present | M-1 | 2000 | 430 | 344 |
| Ex. 7 | P-7 | PVB | Present | Present | M-1 | 2000 | 425 | 338 |
| Ex. 8 | P-8 | PVB | Present | Present | M-1 | 1900 | 430 | 344 |
| Ex. 9 | P-9 | PVB | Present | Present | M-1 | 2100 | 430 | 344 |
| Ex. 10 | P-10 | PVB | Present | Present | M-1 | 2200 | 435 | 350 |
| Ex. 11 | P-11 | PVB | Present | Present | M-1 | 2500 | 430 | 344 |
| Ex. 12 | P-12 | PVB | Present | Present | M-1 | 1900 | 420 | 332 |
| Ex. 13 | P-13 | Acrylic | Absent | Present | M-1 | 1800 | 400 | 322 |
| Ex. 14 | P-14 | Acrylic | Absent | Present | M-1 | 1800 | 400 | 322 |
| Ex. 15 | P-15 | Acrylic | Present | Present | M-1 | 1900 | 430 | 344 |
| Ex. 16 | P-16 | Acrylic | Absent | Present | M-1 | 1600 | 400 | 322 |
| Ex. 17 | P-17 | Acrylic | Present | Present | M-1 | 1700 | 430 | 344 |
| Ex. 18 | P-1 | PVB | Absent | Present | None | 1600 | 395 | 316 |
| Ex. 19 | P-10 | PVB | Present | Present | None | 1700 | 435 | 350 |
| Comp Ex. 1 | #3000-2 | PVB | Absent | Present | M-1 | 500 | 345 | 276 |
| Comp Ex. 2 | TR2000 | Styrene-butadiene copolymer | Present (vulcanized) | Present | M-1 | 2000 | 290 | 232 |
| Comp Ex. 3 | Poly urethane | Poly urethane | Absent | Present | M-1 | 600 | 380 | 304 |
| Comp Ex. 4 | P-1 | PVB | Absent | Absent | M-1 | 2000 | 310 | 256 |

As shown in Table 2, the relief printing plates of Examples 1 to 19 of the invention all had good printing durability, as compared with the relief printing plates of Comparative Examples 1 and 3 that had not been subjected to crosslinking. It was found that all of the Examples had large engraving depths, good engraving sensitivity and high productivity at the time of plate making.

From a comparison of Examples 6 to 12 with Examples 1 to 5, and a comparison of Examples 15, 17 and 19 with Example 13 and Example 14, it is understood that (A) a specific polymer containing S atoms in the molecule provides deeper engraving depth and improved sensitivity.

Furthermore, from a comparison of Example 1 with Comparative Example 1, it is understood that the addition of carbon black results in an enhancement of sensitivity.

It is also understood that when the same relief printing plate precursors are used, the engraving depth may be further improved by using a plate making apparatus that is equipped with a fiber-coupled semiconductor laser and uses FC-LD as a light source.

All publications, patent applications, and technical standards mentioned in this specification are herein incorporated by reference to the same extent as if each individual publication, patent application, or technical standard was specifically and individually indicated to be incorporated by reference.

What is claimed is:

1. A method for producing a relief printing plate, comprising:

providing a relief printing plate precursor for laser engraving, comprising a relief forming layer formed by thermally crosslinking a resin composition comprising (A) a polymer having an ethylenically unsaturated bond in a side chain wherein the polymer is an acrylic resin or a polyvinyl acetal, (B) carbon black, and (C) a thermopolymerization initiator, wherein the (A) polymer having an ethylenically unsaturated bond in a side chain is a polymer having a carbon-sulfur bond between the main chain and the ethylenically unsaturated bond in a side chain, and wherein the ethylenically unsaturated bond is an acryloyl group, a methacryloyl group or a styryl group; and subjecting the relief forming layer in the relief printing plate precursor to laser engraving.

2. The method for producing a relief printing plate according to claim 1, wherein the laser engraving is laser engraving using as a light source a semiconductor laser including a plurality of fibers and having a wavelength of 700 nm to 1200 nm.

3. The method for producing a relief printing plate according to claim 1, wherein the (A) polymer having an ethylenically unsaturated bond in a side chain is a polyvinyl acetal.

4. The method for producing a relief printing plate according to claim 1, wherein the glass transition temperature of the (A) polymer having an ethylenically unsaturated bond in a side chain is from 20° C. to 200° C.

5. The method for producing a relief printing plate according to claim 1, wherein the resin composition further comprises (D) a crosslinking agent.

6. The method for producing a relief printing plate according to claim 5, wherein the (D) crosslinking agent is a compound having an ethylenically unsaturated bond.

* * * * *